US010117757B2

(12) United States Patent
Jimenez et al.

(10) Patent No.: US 10,117,757 B2
(45) Date of Patent: *Nov. 6, 2018

(54) COAXIAL SCREW GEAR SLEEVE MECHANISM

(71) Applicant: Spinex Tec, LLC, Gering, NE (US)

(72) Inventors: Omar F. Jimenez, Gering, NE (US); Nicholas Ransom Powley, St. Paul, MN (US); Andrew G. Fischer, Hopkins, MN (US); Yefim Safris, Golden Valley, MN (US)

(73) Assignee: Spinex Tec, LLC, Gering, NE (US)

( * ) Notice: Subject to any disclaimer, the term of this patent is extended or adjusted under 35 U.S.C. 154(b) by 103 days.

This patent is subject to a terminal disclaimer.

(21) Appl. No.: 15/174,454

(22) Filed: Jun. 6, 2016

(65) Prior Publication Data
US 2016/0356368 A1 Dec. 8, 2016

Related U.S. Application Data

(63) Continuation of application No. 12/841,869, filed on Jul. 22, 2010, now Pat. No. 9,358,125.
(Continued)

(51) Int. Cl.
*A61F 2/00* (2006.01)
*A61F 2/44* (2006.01)
(Continued)

(52) U.S. Cl.
CPC ........ *A61F 2/4465* (2013.01); *A61B 17/7065* (2013.01); *A61F 2/447* (2013.01);
(Continued)

(58) Field of Classification Search
CPC .. F16H 25/2056; F16H 25/2214; F16H 25/20; F16H 2025/209; F16H 2025/2084;
(Continued)

(56) References Cited

U.S. PATENT DOCUMENTS

| 283,218 A | 8/1883 | Ryoke |
| 703,251 A | 6/1902 | Haire |

(Continued)

FOREIGN PATENT DOCUMENTS

| EP | 1342456 A1 | 9/2003 |
| EP | 1881209 A1 | 1/2008 |

(Continued)

OTHER PUBLICATIONS

Notification of Transmittal of the International Search Report and the Written Opinion of the International Searching Authority or the Declaration,Application No. PCT/US2010/042941, dated Apr. 25, 2011.

(Continued)

*Primary Examiner* — Victor L MacArthur
(74) *Attorney, Agent, or Firm* — Carter, DeLuca, Farrell & Schmidt, LLP

(57) ABSTRACT

An improved mechanism for expanding or lifting a device in accordance with various embodiments of the present invention is a coaxial screw gear sleeve mechanism. In various embodiments, coaxial screw gear sleeve mechanisms includes a post with a threaded exterior surface and a corresponding sleeve configured to surround the post, the corresponding sleeve having a threaded interior surface configured to interface with the threaded exterior surface of the post and a geared exterior surface. A drive mechanism can be configured to interface with the geared exterior surface of the sleeve, causing a device utilizing such a mechanism to expand or lift between a collapsed configuration and an expanded configuration.

23 Claims, 19 Drawing Sheets

Related U.S. Application Data

(60) Provisional application No. 61/271,548, filed on Jul. 22, 2009, provisional application No. 61/365,131, filed on Jul. 16, 2010.

(51) Int. Cl.

| | | |
|---|---|---|
| *F16H 25/20* | (2006.01) | |
| *A61B 17/70* | (2006.01) | |
| *A61F 2/46* | (2006.01) | |
| *F16H 25/22* | (2006.01) | |
| *A61B 17/02* | (2006.01) | |
| *A61F 2/38* | (2006.01) | |
| *A61F 2/28* | (2006.01) | |
| *A61F 2/30* | (2006.01) | |
| *A61F 2/34* | (2006.01) | |
| *A61F 2/36* | (2006.01) | |
| *A61F 2/48* | (2006.01) | |
| *A61F 2/50* | (2006.01) | |
| *A61B 17/68* | (2006.01) | |

(52) U.S. Cl.
CPC .......... *A61F 2/4455* (2013.01); *A61F 2/4611* (2013.01); *F16H 25/20* (2013.01); *F16H 25/2056* (2013.01); *F16H 25/2214* (2013.01); *A61B 2017/0256* (2013.01); *A61B 2017/681* (2013.01); *A61F 2/385* (2013.01); *A61F 2/3868* (2013.01); *A61F 2002/2817* (2013.01); *A61F 2002/2835* (2013.01); *A61F 2002/3063* (2013.01); *A61F 2002/3064* (2013.01); *A61F 2002/3082* (2013.01); *A61F 2002/30235* (2013.01); *A61F 2002/30405* (2013.01); *A61F 2002/30434* (2013.01); *A61F 2002/30523* (2013.01); *A61F 2002/30525* (2013.01); *A61F 2002/30556* (2013.01); *A61F 2002/30579* (2013.01); *A61F 2002/30593* (2013.01); *A61F 2002/30601* (2013.01); *A61F 2002/30604* (2013.01); *A61F 2002/30644* (2013.01); *A61F 2002/30645* (2013.01); *A61F 2002/30841* (2013.01); *A61F 2002/30904* (2013.01); *A61F 2002/30925* (2013.01); *A61F 2002/3409* (2013.01); *A61F 2002/3631* (2013.01); *A61F 2002/448* (2013.01); *A61F 2002/4628* (2013.01); *A61F 2002/4629* (2013.01); *A61F 2002/482* (2013.01); *A61F 2002/507* (2013.01); *A61F 2002/5041* (2013.01); *A61F 2002/5069* (2013.01); *A61F 2220/0025* (2013.01); *A61F 2220/0041* (2013.01); *A61F 2230/0069* (2013.01); *A61F 2240/001* (2013.01); *A61F 2250/0009* (2013.01); *A61F 2310/00023* (2013.01); *A61F 2310/00029* (2013.01); *A61F 2310/00796* (2013.01); *A61F 2310/00976* (2013.01); *A61F 2310/00982* (2013.01); *A61F 2310/00988* (2013.01); *A61F 2310/00994* (2013.01); *F16H 2025/209* (2013.01); *F16H 2025/2046* (2013.01); *F16H 2025/2084* (2013.01); *H05K 999/99* (2013.01); *Y10T 29/49* (2015.01); *Y10T 74/18608* (2015.01); *Y10T 74/18672* (2015.01); *Y10T 74/19702* (2015.01); *Y10T 74/19749* (2015.01)

(58) Field of Classification Search
CPC ...... A61F 2/447; A61F 2/4455; A61F 2/4465; A61F 2/4611; A61F 2310/00982; A61F 2310/00976; A61F 2310/00796; A61F 2310/00029; A61F 2310/00023; A61F 2250/0009; A61F 2240/001; A61F 2230/0069; A61F 2220/0041; A61F 2220/0025; A61F 2310/00994; A61F 2310/00988; A61F 2/3868; A61F 2/385; A61F 2002/448; A61F 2002/3631; A61F 2002/3409; A61F 2002/30925; A61F 2002/30904; A61F 2002/4629; A61F 2002/3082; A61F 2002/30645; A61F 2002/30644; A61F 2002/3064; A61F 2002/3063; A61F 2002/30604; A61F 2002/30601; A61F 2002/30593; A61F 2002/30579; A61F 2002/30556; A61F 2002/30525; A61F 2002/30523; A61F 2017/0256; A61F 2002/30434; A61F 2002/30405; A61F 2002/30235; A61F 2002/2835; A61F 2002/2817; A61F 2002/30841; A61F 2002/507; A61F 2002/5069; A61F 2002/5041; A61F 2002/482; A61F 2002/4628; Y10T 74/18672; Y10T 74/18608; Y10T 29/49; Y10T 74/19702; Y10T 74/19749; A61B 17/7065; A61B 2017/0256

USPC .......... 74/89.23, 89.27, 89.34, 89.14, 89.35; 254/425, 89 R, 92, 98, 102, 103

See application file for complete search history.

(56) References Cited

U.S. PATENT DOCUMENTS

| | | |
|---|---|---|
| 811,344 A | 1/1906 | Wands |
| 1,388,836 A | 8/1921 | Ripsch et al. |
| 1,500,859 A | 7/1924 | Wright |
| 1,547,946 A | 7/1925 | Myers |
| 2,106,088 A | 1/1938 | De Tar |
| 2,231,221 A | 2/1941 | Rector |
| 2,453,656 A | 11/1948 | Bullard |
| 2,666,334 A | 1/1954 | Nalle |
| 2,711,105 A | 6/1955 | Williams |
| 2,842,976 A | 7/1958 | Young |
| 2,891,408 A | 6/1959 | Burt, Jr. |
| 3,386,128 A | 6/1968 | Vyvyan |
| 3,449,971 A | 6/1969 | Posh |
| 3,575,475 A | 4/1971 | Boemer |
| 3,596,863 A | 8/1971 | Kaspareck |
| 3,597,938 A | 8/1971 | Hellen et al. |
| 3,700,289 A | 10/1972 | Bilinski et al. |
| 3,700,290 A | 10/1972 | Ensinger |
| 3,708,925 A | 1/1973 | Ainoura |
| 3,709,132 A | 1/1973 | Farrell et al. |
| 3,916,596 A | 11/1975 | Hawley |
| 3,985,000 A | 10/1976 | Hartz |
| 3,988,906 A | 11/1976 | Smith |
| 4,261,211 A | 4/1981 | Haberland |
| 4,396,047 A | 8/1983 | Balkus |
| 4,478,103 A | 10/1984 | Benjamin |
| 4,516,303 A | 5/1985 | Kloster |
| 4,528,864 A | 7/1985 | Craig |
| 4,559,717 A | 12/1985 | Scire et al. |
| 4,630,495 A | 12/1986 | Smith |
| 4,691,586 A | 9/1987 | van Leijenhorst et al. |
| 4,694,703 A | 9/1987 | Routson |
| 4,869,552 A | 9/1989 | Tolleson et al. |
| 5,133,108 A | 7/1992 | Esnault |
| 5,172,442 A | 12/1992 | Bartley et al. |
| 5,181,371 A | 1/1993 | DeWorth |
| 5,196,857 A | 3/1993 | Chiappetta et al. |
| 5,198,932 A | 3/1993 | Takamura |
| 5,222,986 A | 6/1993 | Wright |
| 5,313,852 A | 5/1994 | Arena |
| 5,374,556 A | 12/1994 | Bennett et al. |
| 5,439,377 A | 8/1995 | Milanovich |
| 5,445,471 A | 8/1995 | Wexler et al. |
| 5,645,599 A | 7/1997 | Samani |
| 5,664,457 A | 9/1997 | Nejati |
| 5,904,479 A | 5/1999 | Staples |

(56) References Cited

U.S. PATENT DOCUMENTS

| | | | |
|---|---|---|---|
| 5,960,670 A | 10/1999 | Iverson et al. |
| 5,980,252 A | 11/1999 | Samchukov et al. |
| 5,988,006 A | 11/1999 | Fleytman |
| 6,045,579 A | 4/2000 | Hochshuler et al. |
| 6,056,491 A | 5/2000 | Hsu |
| 6,136,031 A | 10/2000 | Middleton |
| 6,315,797 B1 | 11/2001 | Middleton |
| 6,350,317 B1 | 2/2002 | Hao et al. |
| 6,378,172 B1 | 4/2002 | Schrage |
| 6,395,035 B2 | 5/2002 | Bresina et al. |
| 6,454,806 B1 | 9/2002 | Cohen et al. |
| 6,484,608 B1 | 11/2002 | Ziavras |
| 6,517,772 B1 | 2/2003 | Woolf |
| 6,554,526 B1 | 4/2003 | Egelandsdal |
| 6,616,695 B1 | 9/2003 | Crozet et al. |
| 6,641,614 B1 | 11/2003 | Wagner et al. |
| 6,719,796 B2 | 4/2004 | Cohen et al. |
| 6,752,832 B2 | 6/2004 | Neumann |
| 6,772,479 B2 | 8/2004 | Hinkley et al. |
| 6,802,229 B1 | 10/2004 | Lambert |
| 6,808,537 B2 | 10/2004 | Michelson |
| 6,863,673 B2 | 3/2005 | Gerbec et al. |
| 6,932,844 B2 | 8/2005 | Ralph et al. |
| 6,953,477 B2 | 10/2005 | Berry |
| 7,018,415 B1 | 3/2006 | McKay |
| 7,051,610 B2 | 5/2006 | Stoianovici et al. |
| 7,070,598 B2 | 7/2006 | Lim et al. |
| 7,201,751 B2 | 4/2007 | Zucherman et al. |
| 7,273,373 B2 | 9/2007 | Horiuchi |
| 7,308,747 B2 | 12/2007 | Smith et al. |
| 7,316,381 B2 | 1/2008 | Hacker et al. |
| 7,410,201 B1 | 8/2008 | Wilson et al. |
| 7,425,103 B2 | 9/2008 | Perez-Sanchez |
| 7,435,032 B1 | 10/2008 | Murphey et al. |
| 7,584,682 B2 | 9/2009 | Hsiao |
| 7,611,538 B2 | 11/2009 | Belliard et al. |
| 7,632,281 B2 | 12/2009 | Errico et al. |
| 7,674,296 B2 | 3/2010 | Rhoda et al. |
| 7,682,376 B2 | 3/2010 | Trieu |
| 7,708,779 B2 | 5/2010 | Edie |
| 7,712,389 B2 | 5/2010 | Wang |
| 7,753,958 B2 | 7/2010 | Gordon et al. |
| 7,758,645 B2 | 7/2010 | Studer |
| 7,758,648 B2 | 7/2010 | Castleman et al. |
| 7,892,285 B2 | 2/2011 | Viker |
| 7,896,919 B2 | 3/2011 | Belliard et al. |
| 7,947,078 B2 | 5/2011 | Siegal |
| 7,985,256 B2 | 7/2011 | Grotz et al. |
| 8,070,813 B2 | 12/2011 | Grotz et al. |
| 8,088,163 B1 | 1/2012 | Kleiner |
| 8,192,495 B2 | 6/2012 | Simpson et al. |
| 2003/0077110 A1 | 4/2003 | Knowles |
| 2003/0233145 A1 | 12/2003 | Landry et al. |
| 2004/0111157 A1 | 6/2004 | Ralph et al. |
| 2004/0225364 A1 | 11/2004 | Richelsoph et al. |
| 2005/0000228 A1 | 1/2005 | De Sousa et al. |
| 2005/0033431 A1 | 2/2005 | Gordon et al. |
| 2005/0095384 A1 | 5/2005 | Wittmeyer |
| 2005/0113924 A1 | 5/2005 | Buttermann |
| 2005/0175406 A1 | 8/2005 | Perez-Sanchez |
| 2006/0004447 A1 | 1/2006 | Mastrorio et al. |
| 2006/0004455 A1 | 1/2006 | Leonard et al. |
| 2006/0025862 A1 | 2/2006 | Villiers et al. |
| 2006/0129244 A1 | 6/2006 | Ensign |
| 2006/0149385 A1 | 7/2006 | McKay |
| 2006/0184171 A1 | 8/2006 | Biedermann et al. |
| 2006/0247781 A1 | 11/2006 | Francis |
| 2006/0293752 A1 | 12/2006 | Moumene et al. |
| 2007/0049943 A1 | 3/2007 | Moskowitz et al. |
| 2007/0083267 A1 | 4/2007 | Miz et al. |
| 2007/0129730 A1 | 6/2007 | Woods et al. |
| 2007/0185577 A1 | 8/2007 | Malek |
| 2007/0191954 A1 | 8/2007 | Hansell et al. |
| 2007/0191958 A1 | 8/2007 | Abdou |
| 2007/0198089 A1 | 8/2007 | Moskowitz et al. |
| 2007/0219634 A1 | 9/2007 | Greenhalgh et al. |
| 2007/0222100 A1 | 9/2007 | Husted et al. |
| 2007/0250171 A1 | 10/2007 | Bonin |
| 2007/0255415 A1 | 11/2007 | Edie et al. |
| 2007/0282449 A1 | 12/2007 | de Villiers et al. |
| 2007/0293329 A1 | 12/2007 | Glimpel et al. |
| 2007/0293948 A1 | 12/2007 | Bagga et al. |
| 2008/0026903 A1 | 1/2008 | Flugrad et al. |
| 2008/0077246 A1 | 3/2008 | Fehling et al. |
| 2008/0091211 A1 | 4/2008 | Gately |
| 2008/0100179 A1 | 5/2008 | Ruggeri et al. |
| 2008/0140207 A1 | 6/2008 | Olmos et al. |
| 2008/0147194 A1 | 6/2008 | Gratz et al. |
| 2008/0161920 A1 | 7/2008 | Melkent |
| 2008/0161931 A1 | 7/2008 | Perez-Cruet et al. |
| 2008/0168855 A1 | 7/2008 | Giefer et al. |
| 2008/0188941 A1 | 8/2008 | Grotz |
| 2008/0210039 A1 | 9/2008 | Brun |
| 2008/0221694 A1 | 9/2008 | Warnick et al. |
| 2008/0234736 A1 | 9/2008 | Trieu et al. |
| 2008/0281423 A1 | 11/2008 | Sheffer et al. |
| 2008/0292392 A1 | 11/2008 | Voellmer |
| 2008/0319487 A1 | 12/2008 | Fielding et al. |
| 2009/0012564 A1 | 1/2009 | Chirico et al. |
| 2009/0076614 A1 | 3/2009 | Arramon |
| 2009/0164017 A1 | 6/2009 | Sommerich et al. |
| 2009/0210061 A1 | 8/2009 | Sledge |
| 2009/0222100 A1 | 9/2009 | Cipoletti et al. |
| 2009/0234362 A1 | 9/2009 | Blain et al. |
| 2009/0306672 A1 | 12/2009 | Reindel et al. |
| 2010/0004688 A1 | 1/2010 | Maas et al. |
| 2010/0076557 A1 | 3/2010 | Miller |
| 2010/0082109 A1 | 4/2010 | Greenhalgh et al. |
| 2010/0094305 A1 | 4/2010 | Chang et al. |
| 2010/0185291 A1 | 7/2010 | Jimenez et al. |
| 2010/0192715 A1 | 8/2010 | Vauchel et al. |
| 2010/0209184 A1 | 8/2010 | Jimenez et al. |
| 2011/0054616 A1 | 3/2011 | Kamran et al. |
| 2011/0093075 A1 | 4/2011 | Duplessis et al. |
| 2011/0112644 A1 | 5/2011 | Zilberstein et al. |
| 2011/0160861 A1 | 6/2011 | Jimenez et al. |
| 2011/0270398 A1 | 11/2011 | Grotz et al. |
| 2012/0116518 A1 | 5/2012 | Grotz et al. |
| 2012/0158071 A1 | 6/2012 | Jimenez et al. |
| 2012/0323329 A1 | 12/2012 | Jimenez et al. |
| 2013/0053966 A1 | 2/2013 | Jimenez et al. |

FOREIGN PATENT DOCUMENTS

| | | |
|---|---|---|
| FR | 2372998 A1 | 6/1978 |
| JP | 2004301135 A | 10/2004 |
| JP | 2008208932 A | 9/2008 |
| WO | 2004026188 A2 | 4/2004 |
| WO | 2004109155 A1 | 12/2004 |
| WO | 2005081330 A2 | 9/2005 |
| WO | 2006094535 A1 | 9/2006 |
| WO | 2006116052 A2 | 11/2006 |
| WO | 2006125329 A1 | 11/2006 |
| WO | 2007002583 A2 | 1/2007 |
| WO | 2007028140 A2 | 3/2007 |
| WO | 2007111979 A2 | 10/2007 |
| WO | 2008137192 A1 | 11/2008 |
| WO | 2009018349 A2 | 2/2009 |
| WO | 2010078520 A2 | 7/2010 |

OTHER PUBLICATIONS

International Search Report, Application No. PCT/US2010/042915, dated Apr. 22, 2011.

Application and File History for U.S. Appl. No. 13/189,410, Inventors: Jimenez et al, filed Jul. 22, 2011.

Application and File History for U.S. Appl. No. 13/591,463, Inventors: Jimenez et al, filed Aug. 22, 2012.

Application and File History for U.S. Appl. No. 13/661,534, filed Oct. 26, 2012, Inventors: Jimenez et al.

International Search Report and Written Opinion of the International Searching Authority or the Declaration dated Sep. 27, 2010,

(56) References Cited

OTHER PUBLICATIONS

International Application No. PCT/US2009/069876, filed Dec. 30, 2009, 12 pages.
International Search Report and Written Opinion of the International Searching Authority or the Declaration dated Nov. 29, 2010, International Application No. PCT/US2009/069958, filed Dec. 31, 2009, 9 pages.
Wenzel Spine, Inc., VariLift.RTM.-L Expandable Interbody Fusion Device: A proven solution for stand-alone fusion, Product Overview, 12 pages, .COPYRGT. 2010.
Peter A. Halverson, et al., Tension-based Multi-stable Compliant: Rolling-contact Elements, Department of Mechanical Engineering, Brigham Young University, Provo UT, USA 84602 (34 pages), 2007.
Just L. Herder, Force Directed Design of Laparoscopic Forceps, 1998, ASME Design Engineering Technical Conference (8 pages).
Alexander H. Slocum, Fundamentals of Design (2005).
Amelie Jeanneau, et al., A Compliant Rolling Contact Joint and its Application in a 3-DOF Planar Parallel Mechanism with Kinematic Analysis, ASME (2004) Design Engineering Technical Conferences (9 pages).
Application and File History of U.S. Appl. No. 12/651,266, Inventors Jimenez et al., filed Dec. 31, 2009.
Application and File History of U.S. Appl. No. 12/650,994, Inventors Jimenez et al., filed Dec. 31, 2009.
Application and File History of U.S. Appl. No. 12/841,465, Inventors Jimenez et al., filed Jul. 22, 2010.
Application and File History of U.S. Appl. No. 12/407,608, Inventors Omar F. Jimenez, filed Mar. 19, 2009.
W. Kiisswetter, A Supplementary Instrumentation for Posterior Fusion of Spine in Scoliosis, Archives of Orthopedic Traumatic Surgery, 1980, 1 page.
Chou et al., Efficacy of Anterior Cervical Fusion: Comparison of Titanium Cages, polyetheretherketone (PEEK) cages and autogenous bone grafts, Journal of Clinical Neuroscience, 2008, pp. 1240-1245.
Hunter et al., Overview of Medical Devices, Department of Radiology, University of Arizona, Aug. 2001, pp. 89-140, vol. 30, No. 4, ISSN: 0363-0188.
Medtronic Sofamor Danek USA, Inc., Capstone Instrument Set Technique, http://www.mtortho.com/public/capstone.pdf, .COPYRGT. 2005, 25 pages.
Medtronic, Capstone Peek Spinal System Surgical Technique, http://www.mtortho.com/public/capstone.sub.-peek.sub.-st.pdf, .COPYRGT. 2009, 36 pages.
Japanese Application No. 2012-521784, JP Office Action dated Feb. 18, 2014, 8 pages.
PCT/US2013/067070, PCT Written Opinion/Search Report dated Feb. 27, 2014, 14 pages.

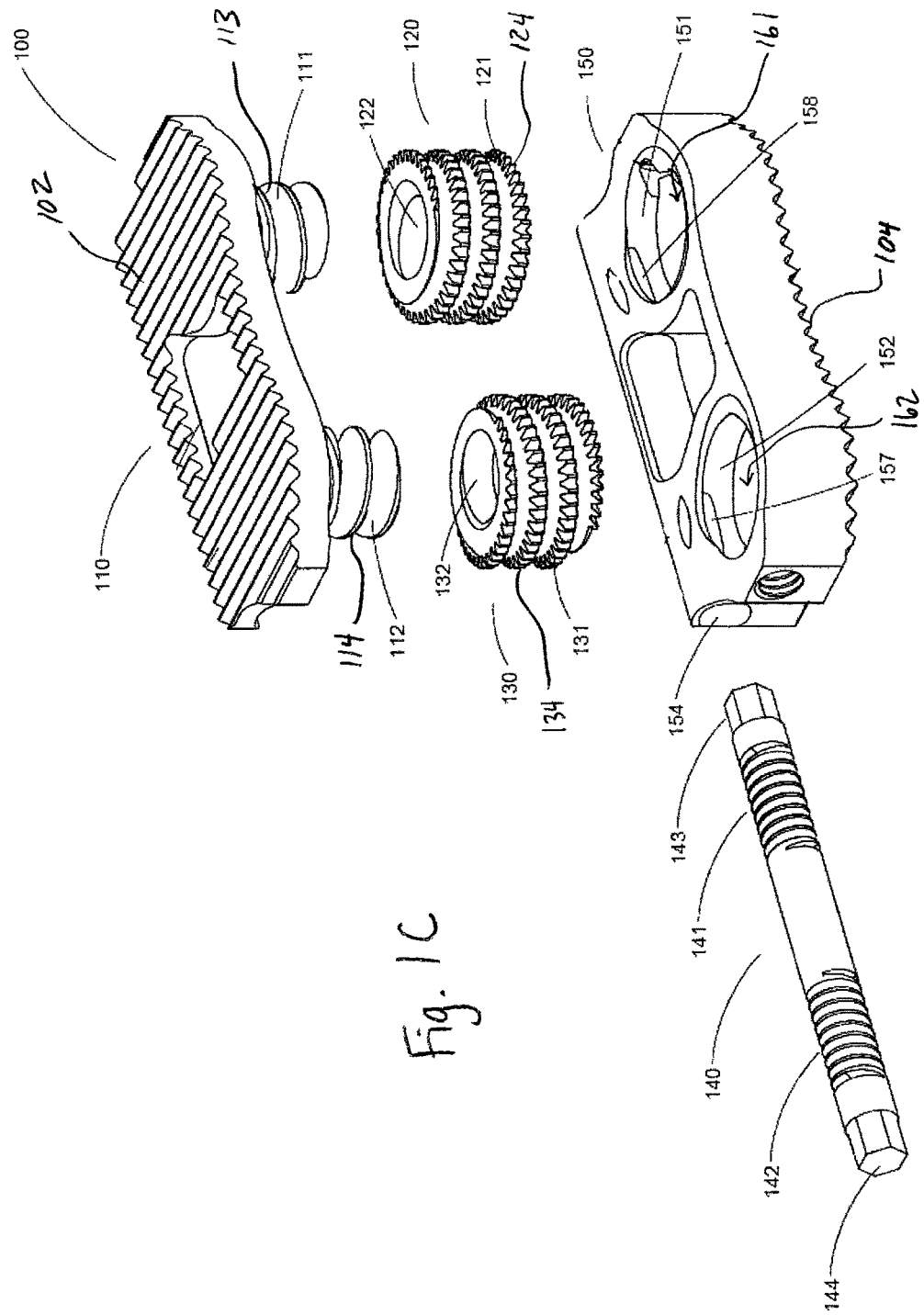

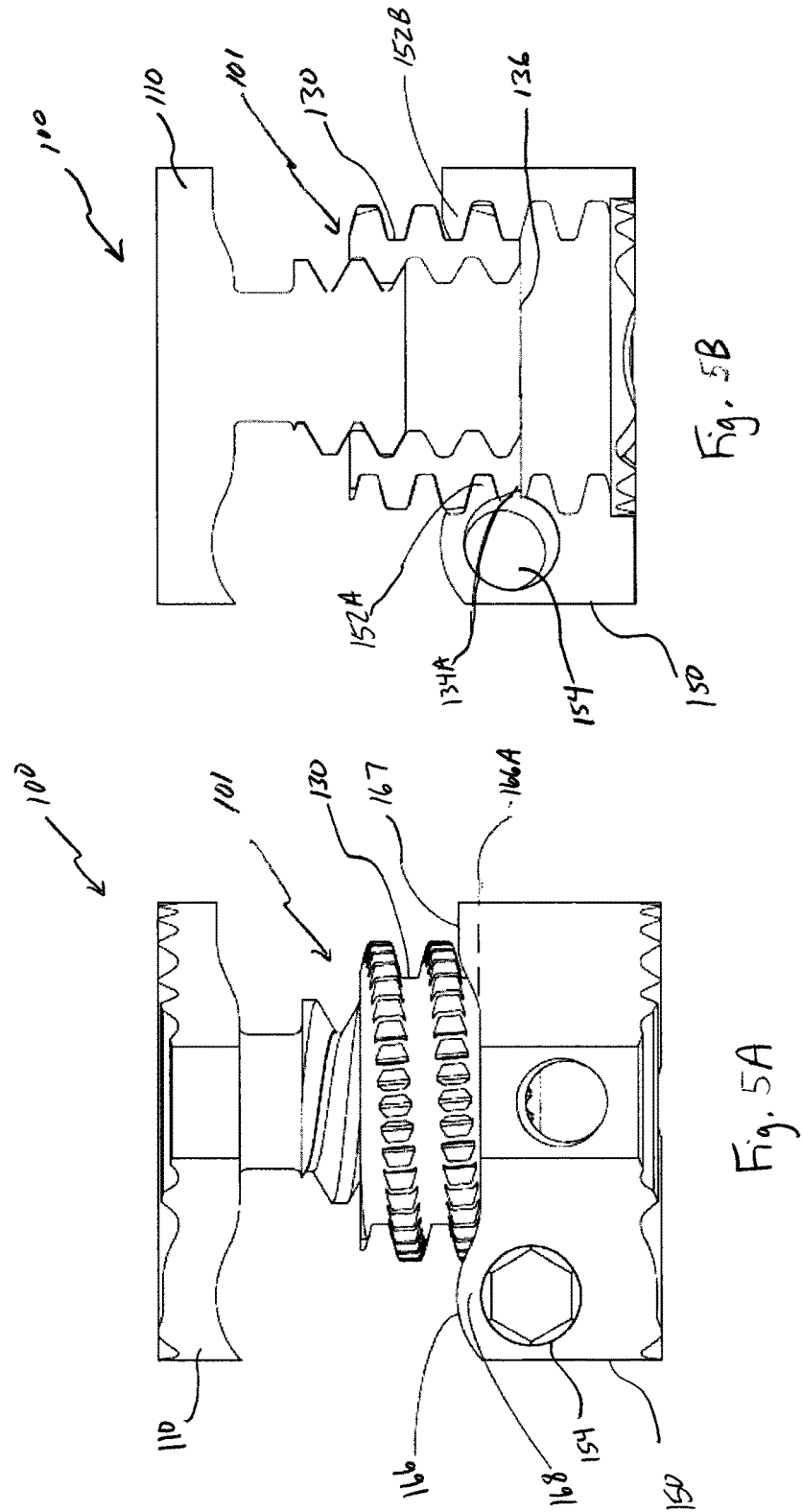

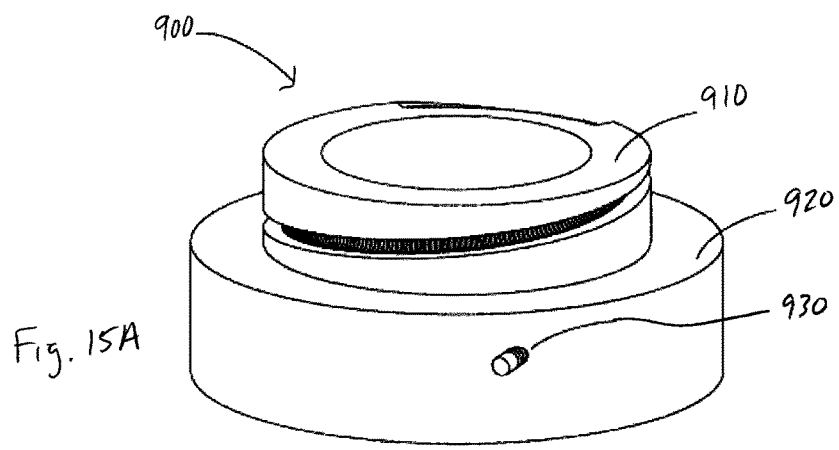
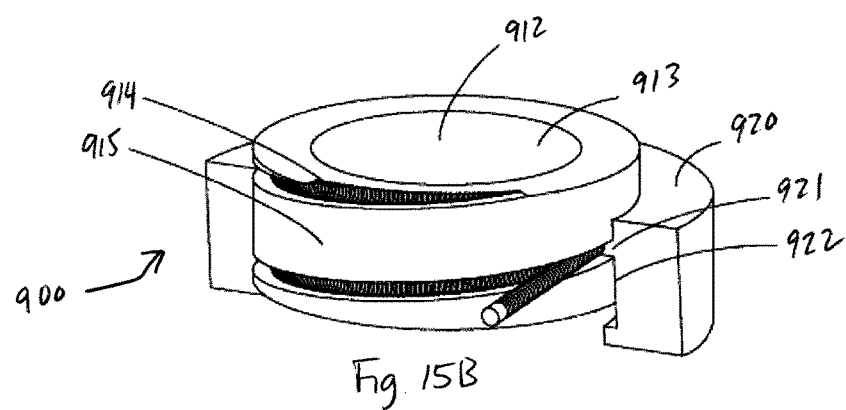
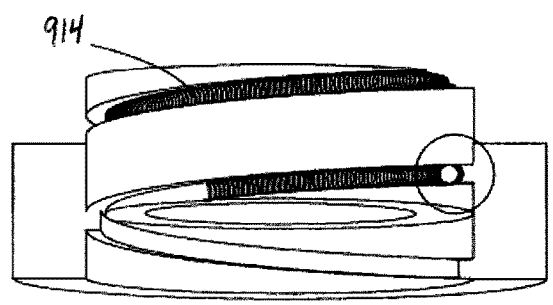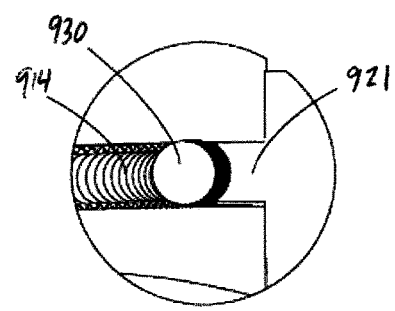

COAXIAL SCREW GEAR SLEEVE MECHANISM

RELATED APPLICATION

This application is a continuation of U.S. application Ser. No. 12/841,869, fled Jul. 22, 2010, now U.S. Pat. No. 9,38,125, claims the benefit of U.S. Provisional Application No. 61/271,548, filed Jul. 22, 2009, and U.S. Provisional Application No. 61/365,131,filed Jul. 16, 2010, each of which is hereby fully incorporated herein by reference.

FIELD OF THE INVENTION

The present invention relates to mechanisms for expanding or lifting between a compressed configuration and an expanded configuration. More specifically, the present invention relates to a coaxial screw gear sleeve mechanism.

BACKGROUND OF THE INVENTION

Many devices use various mechanisms to expand or lift the device from a compressed configuration to an expanded configuration. The goal of such mechanisms is typically to provide a device with the greatest difference between its compressed configuration and its expanded configuration, while still providing sufficient strength to provide a stable device that can support whatever type of load that may be placed on the device. However, many such mechanisms either require a large compressed configuration, limited expansion from the compressed configuration to the expanded configuration, and/or lack the strength to keep the device stable under loading conditions.

Accordingly, it would be desirable to provide a mechanism that can be used for expanding or lifting a device that provides for a small compressed configuration and a large expansion to an expanded configuration, while possessing sufficient strength to provide a stable base under loading conditions.

SUMMARY OF THE INVENTION

An improved mechanism for expanding or lifting a device in accordance with various embodiments of the present invention is a coaxial screw gear sleeve mechanism. In various embodiments, coaxial screw gear sleeve mechanism includes a post with a threaded exterior surface and a corresponding sleeve configured to surround the post, the corresponding sleeve having a threaded interior surface configured to interface with the threaded exterior surface of the post and a geared exterior surface. A drive mechanism can be configured to interface with the geared exterior surface of the sleeve, causing a device utilizing such a mechanism to expand or lift between a collapsed configuration and an expanded configuration.

In one embodiment, a coaxial screw gear sleeve mechanism includes a post with a threaded exterior surface and a corresponding sleeve configured to surround the post. The sleeve can have a threaded interior surface configured to interface with the threaded exterior surface of the post and a geared exterior surface. The device can further include a drive mechanism having a surface configured to interface with and drive the geared exterior surface of the sleeve, which causes an expansion of the sleeve relative to the drive mechanism and the post relative to the sleeve.

In another embodiment, a method of expanding a jacking or lifting mechanism includes providing a coaxial screw gear sleeve mechanism including a threaded post, a corresponding sleeve having an interior thread mating with the threaded post and an exterior gear mating with a drive mechanism. The mechanism is expanded or lifted from a collapsed configuration to an expanded configuration by operating the drive mechanism to rotate the sleeve relative to the post, thereby simultaneously expanding the sleeve relative to the drive mechanism and the post relative to the sleeve.

The above summary of the various embodiments of the invention is not intended to describe each illustrated embodiment or every implementation of the invention. This summary represents a simplified overview of certain aspects of the invention to facilitate a basic understanding of the invention and is not intended to identify key or critical elements of the invention or delineate the scope of the invention.

BRIEF DESCRIPTION OF THE DRAWINGS

The invention may be more completely understood in consideration of the following detailed description of various embodiments of the invention in connection with the accompanying drawings, in which:

FIG. 1C is an exploded view of the device of FIG. 1A.

FIG. 5A is an end view of a device employing a coaxial screw gear sleeve mechanism according to an embodiment of the present invention.

FIG. 5B is a cross-sectional end view of the device of FIG. 5A taken looking into the page.

FIG. 15A is a perspective view of a expandable device employing a coaxial screw gear sleeve mechanism according to an embodiment of the present invention.

FIG. 15B is a partial view of the device of FIG. 15A.

FIG. 15C is a partial view of the device of FIG. 15A.

FIG. 15D is a partial view of the device of FIG. 15A.

Figure 1A:
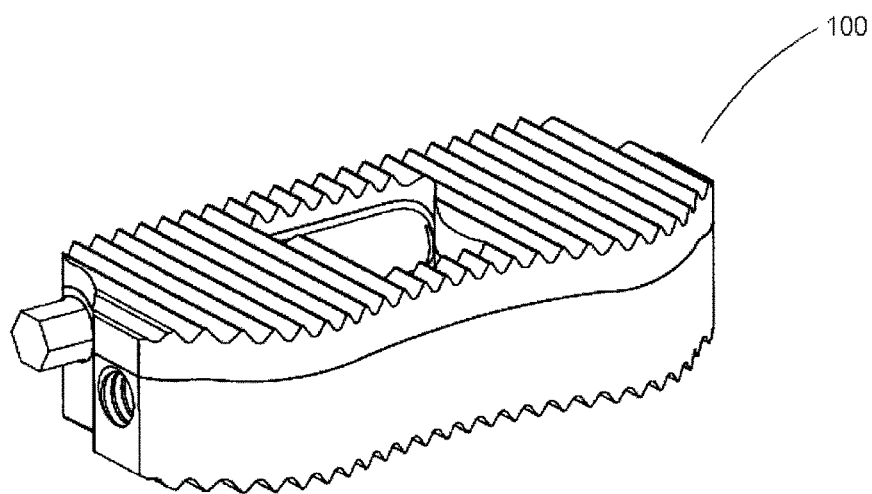
FIG. 1A is perspective view of a device employing a coaxial screw gear sleeve mechanism according to an embodiment of the present invention in a collapsed configuration.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE DRAWINGS

In the following detailed description of the present invention, numerous specific details are set forth in order to provide a thorough understanding of the present invention. However, one skilled in the art will recognize that the present invention may be practiced without these specific details. In other instances, well-known methods, procedures, and components have not been described in detail so as to not unnecessarily obscure aspects of the present invention.

Figure 1B:
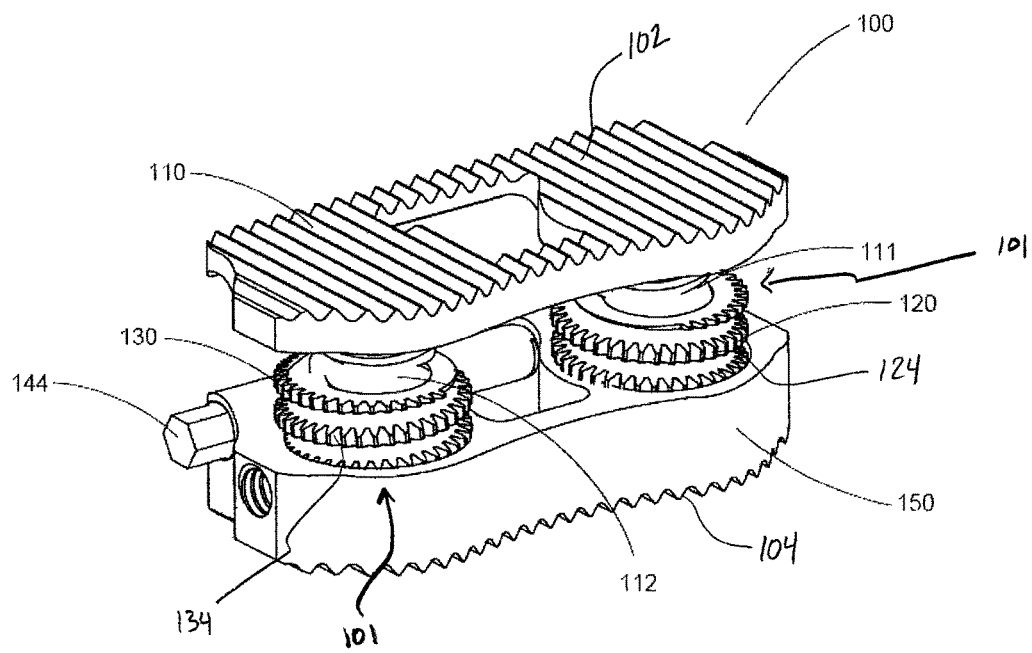
FIG. 1B is a perspective view of the device of FIG. 1A in an expanded configuration.

Referring to FIGS. 1A-1C, there can be seen a device 100 that utilizes a pair of coaxial screw gear sleeve mechanisms 101 according to an embodiment of the present invention. FIG. 1A shows the device 100 and coaxial screw gear sleeve mechanisms 101 in a fully compressed configuration, FIG. 1B shows a fully expanded configuration, and FIG. 1C shows an exploded view of the device 100. Device 100 includes a first member 110 having an outer surface 102 and a second member 150 having an outer surface 104.

Device 100 can also include a pair of coaxial screw gear sleeve mechanisms 101. Coaxial screw gear sleeve mechanisms 101 include respective threaded post members 111, 112 extending from first member 110 and a pair of threaded geared sleeves 120, 130 configured to surround the post members 111, 112. Threaded post members 111, 112 can have threads 113, 114 defined on an exterior surface thereof. Threaded geared sleeves 120, 130 can have both interior threads 122, 132 configured to interface with the threads 113, 114 of threaded post members 111, 112 and exterior threads 121, 131. In one embodiment, both the exterior 121 and interior 122 threads of one of the sleeves 120 are of an opposite hand to the threads 131, 132 of the other sleeve 130. External threads 121, 131 of sleeves 120, 130 can have gear teeth 124, 134 cut into the thread. In one embodiment, the gear teeth 124, 134 are not cut down to the root, or minor diameter, of the threads 121, 131 in order to maximize the strength of the threads. In the compressed configuration, threaded geared sleeves 120, 130 can fit within sleeve openings 161, 162 in second member 150. Openings 161, 162 can include threaded portions 151, 152 that mesh with exterior threads 121, 131 of threaded geared sleeves 120, 130. In some embodiments, as pictured, threaded geared sleeves 120, 130 can be substantially solid. In other embodiments, threaded geared sleeves can include one or more slots through the sleeve for mass reduction and material savings.

The coaxial screw gear sleeve mechanisms 101 can be actuated, and the device 100 therefore expanded, with the aid of a worm 140 that extends through a worm aperture 154 in the device 100. The worm 140 can have first 142 and second 141 opposing threaded sections configured to interface with the exterior threads having gear teeth 124, 134 of threaded geared sleeves 120, 130 through a pair of apertures 157, 158 in threaded portions 151, 152 of sleeve openings 161, 162. The worm 140 can include a hex 143, 144 at each end of the worm 140 that allows it to be driven by an external device.

Figure 1D:
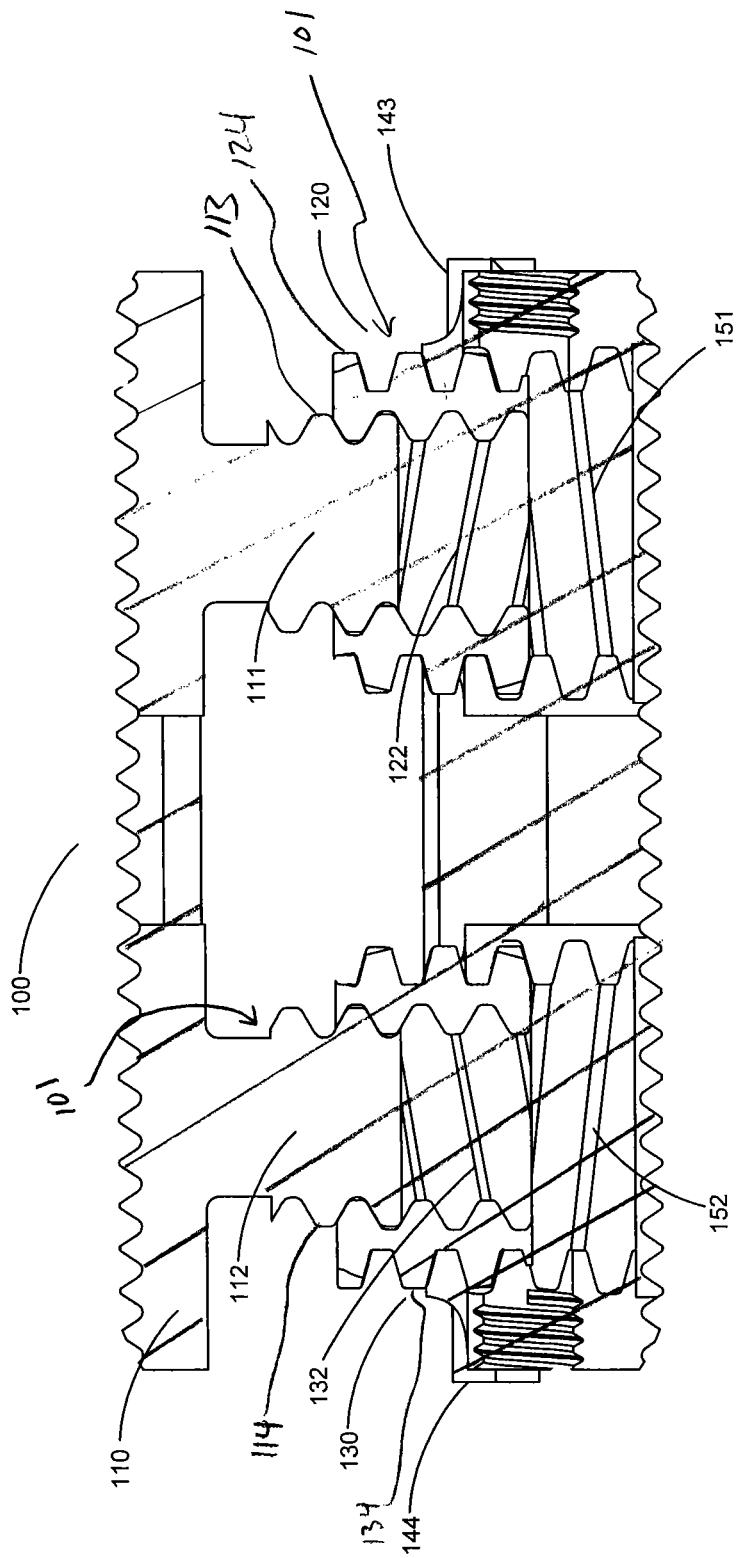
FIG. 1D is a partial sectional view of the device of FIG. 1A.

A partial sectional view of a pair of coaxial screw gear sleeve mechanisms 101 in use with a device 100 in FIG. 1D helps illustrate how a device can employ multiple coaxial screw gear sleeve mechanisms as telescoping mechanisms utilizing the threaded post members 111, 112, threaded geared sleeves 120, 130 and the worm 140 to expand the first member 110 and second member 150 relative to each other. By turning hex 144 counterclockwise, and therefore the worm 140 counterclockwise, first threaded section 142 of worm 140 pulls the gear teeth 134 of threaded geared sleeve 130 towards the hex head 144. This causes the sleeve 130 to translate upward from the second member 150 and worm 140 along internal threads 152. As the sleeve 130 rotates while it translates upward, the threaded post member 112 extending from the first member 110, which is unable to turn, also translates upward with respect to the sleeve 130 and the second member 150. This second translation results from the opposite handed external threads 114 of the threaded post member 112 being driven by the matching internal threads 132 of the sleeve 130. The same mechanics are occurring on the other side of the device with oppositely threaded sleeve 120 having external threads 121 and internal threads 122, post member 111 having external threads 113 and second threaded section 141 of worm 140.

Because the threads for like components for each device are opposite handed, the threads 142 on one side of the worm 140 will be pulling the gear teeth 134 of the threaded geared sleeve 130 while the threads 141 on the other side of the worm 140 will be pushing the gear teeth 124 on the other sleeve 120, or vice versa depending on the direction of rotation of the worm 140. These opposing forces applied to the worm 140 by the threaded geared sleeves 120, 130 are carried in either tension or compression by the worm 140.

Alternative drive mechanisms to worm drive for actuating coaxial screw gear sleeve mechanisms include piezoelectric actuators and any momentum imparting collision mechanism or configuration.

Figure 2A:
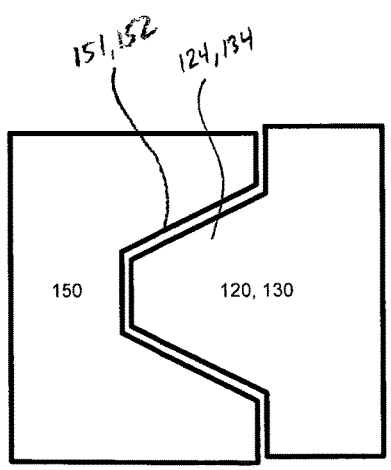
FIG. 2A is a partial side view of a coaxial screw gear sleeve mechanism according to an embodiment of the present invention.
Figure 2B:
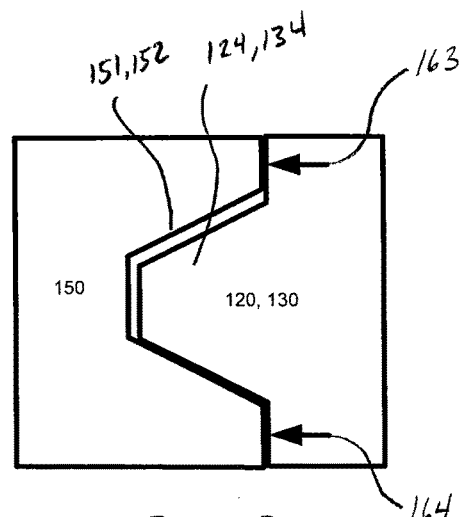
FIG. 2B is a partial side view of the coaxial screw gear sleeve mechanism of FIG. 2A.
Figure 3A:
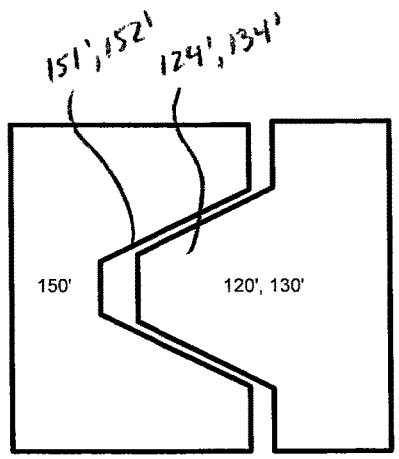
FIG. 3A is a partial side view of a coaxial screw gear sleeve mechanism according to an embodiment of the present invention.
Figure 3B:
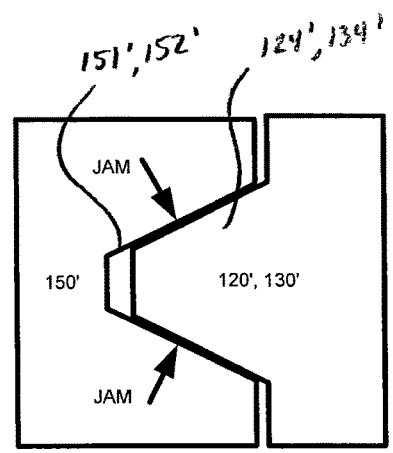
FIG. 3B is a partial side view of the coaxial screw gear sleeve mechanism of FIG. 3A.

Referring now to FIGS. 2A and 2B, a preferred fit of gear teeth 124, 134 of threaded geared sleeves 120, 130 with a cooperating thread such as internal threaded portions, 151, 152 of second member 150 is shown. As the gear teeth 124, 134 are thrust towards the internal threads 151, 152 of the second member 150 by the worm, the load between the gear teeth 124, 134 and threads 151, 152 is balanced by the bearing surfaces 163, 164 between the components, which results in the ability of the device 100 to expand under or lift a substantial load. This fit between the gear teeth 124, 134 and the internal threads 151, 152 can be contrast with the fit shown in FIGS. 3A and 3B. In those figures, when the gear teeth 124', 134' of the threaded geared sleeves 120', 130' are thrust towards the internal threads 151', 152' of the second member 150', the force is not balanced by bearing surfaces as in FIG. 2B, but by the force the internal threads 151', 152' apply to the gear teeth 124', 134'. This can result in the gear teeth 124', 134' acting as a wedge and becoming jammed against the internal threads 151', 152', which dramatically reduces the ability of the coaxial screw gear sleeve mechanisms to expand under or lift substantial loads and makes the mechanism more sensitive to friction between components. Optionally, a liquid or gas lubricant, such as silicon lubricant, may be used to reduce friction in the mechanism. Saline may also be used as a lubricant.

It should be noted that although the threads depicted in the Figures are all screw threads in the form of projecting helical ribs, "thread" for the purposes of the present invention can also refer to any other mechanism that translates rotational force into translational or longitudinal movement. For example, in some embodiments threads can be comprised of a recirculating or spiral arrangement of bearings or any other low friction arrangement, such as cooperating magnets.

In one embodiment, the height of a device 100 utilizing coaxial gear sleeve mechanisms 101 between the bearing surfaces 102, 104 in the fully compressed configuration is 6.5 millimeters and the maximum fully expanded height is 12 millimeters, thus providing a very large amount of expansion relative to the initial height of the device. The maximum height is defined by the largest height at which the device can meet the dynamic compressive, shear, and torsional requirements for the given use of the device. Variables that determine this height include the width of the threaded geared sleeves, which is limited by the desired width of the device, and the material from which the device is made. With regard to the material for the device, materials with higher fatigue performance allow the maximum height of the device to be taller even with a narrower width.

Once expanded, coaxial gear sleeve mechanisms 101 do not require a locking mechanism to maintain the desired height, even under loading conditions. This is because, when driven backwards, the mechanism exhibits a very high gear ratio which causes even the slightest friction in the system to overwhelm any amount of compression, torsion, or shear loading that might be applied to the device. In dynamic testing in shear, torsion, and compression, the maximum amount by which the height of one embodiment of the device that had a maximum expansion of 5.5 millimeters changed was by approximately 0.01 millimeter. The device 100, because height can be maintained at any point along the threaded geared sleeves, therefore also exhibits very high resolution height control, on the order of 1 micrometer.

Figure 4A:
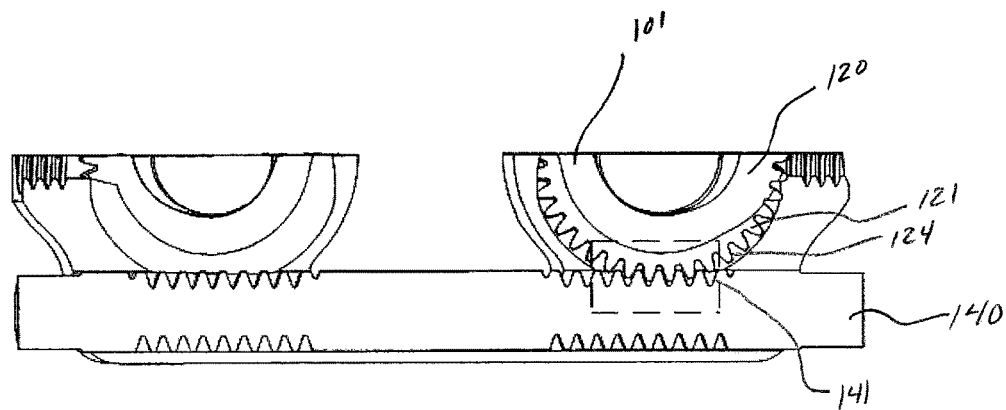
FIG. 4A is a partial top view of a coaxial screw gear sleeve mechanism according to an embodiment of the present invention.
Figure 4B:
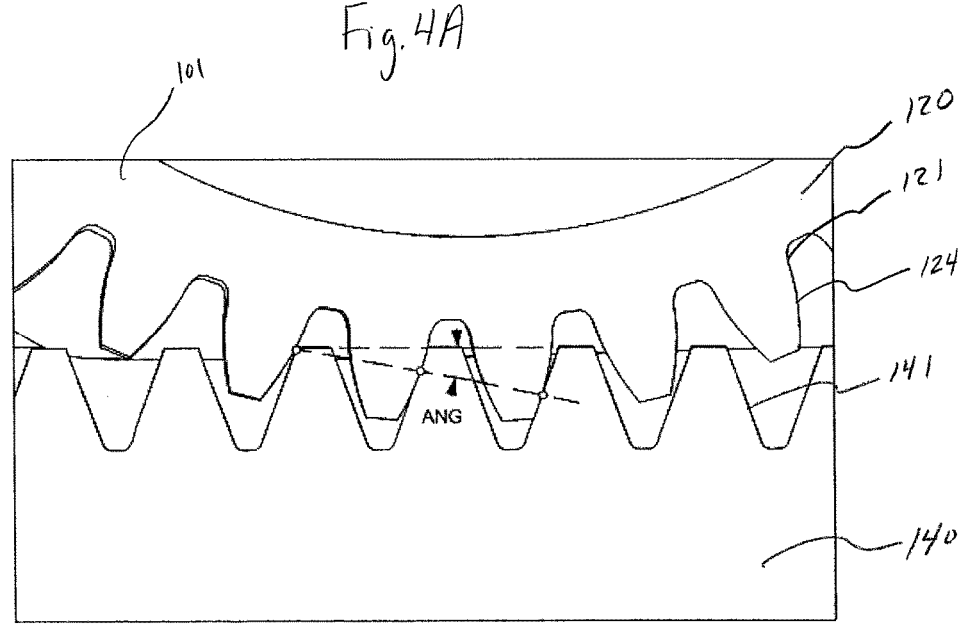
FIG. 4B is a partial top view of the coaxial screw gear sleeve mechanism of FIG. 4A.

In one embodiment, the external threads 121, 131 and gear teeth 124, 134 on the threaded geared sleeves 120, 130 can be substantially trapezoidal in shape. In one embodiment, the thread is a trapezoidal 8 millimeter by 1.5 millimeter metric thread. A trapezoidal design enables a relatively large gear tooth size and, accordingly, a larger area over which the expansion or lifting loading is distributed. Additionally, with precise manufacturing, multiple gear teeth 124, 134 on the threaded geared sleeves 120, 130 can be engaged by the worm 140 at the same time along the pressure angle ANG, as shown in FIGS. 4A and 4B. Distributing the expansion load over multiple teeth of the sleeves 120, 130 and the worm 140 is critical to achieve the minimum device size while providing a maximum amount of expansion or lift and load capacity.

In one embodiment, the coaxial gear sleeve mechanisms 101 can be used with a device 100 having a strengthened second member 150 as shown in FIGS. 5A and 5B. This can be done by lowering the worm aperture 154, and therefore the worm 140, such that when the device 100 is expanded to its full height, the worm 140 engages a full gear tooth 134A on the threaded geared sleeve 130 closest to the bottom 136 of the threaded geared sleeve 130. This allows a top surface 166 of the second member 150 to be lowered, which allows the first member 110 to be thicker, and therefore stronger, while maintaining the same initial height In addition, this allows the material 168 between the top surface 166 of the second member 150 and the worm aperture 154 to be made thicker. A further advantage of this configuration is that at least one full internal thread 152A of the second member 150 is in engagement with the threaded geared sleeve 134 when the device is fully expanded. In such a configuration, an additional thickness 167 can be added to the side of second member 150 opposite of the worm aperture 154 to what was previously described as the top surface 166A of that side of the second member 150. This allows for a full internal thread 152B to engage the threaded geared sleeve 130 on the side opposite of internal thread 152A. By capturing the threaded geared sleeve with a full thread on both sides, when the device is loaded with shear and torsion, a maximum amount of material is resisting the load, which minimizes the resulting stress and increases the fatigue life of the device 100.

Figure 6A:
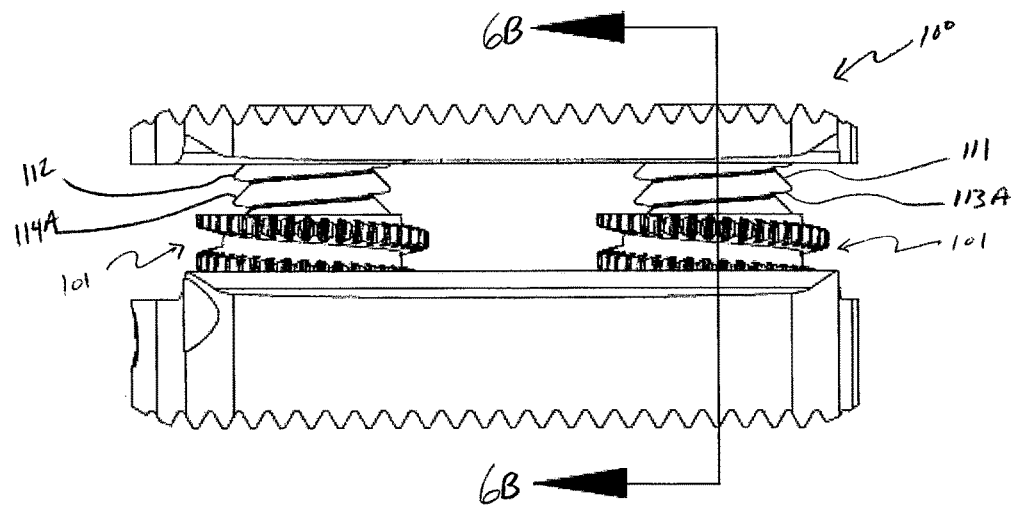
FIG. 6A is a front view of a device employing a coaxial screw gear sleeve mechanism according to an embodiment of the present invention.
Figure 6B:
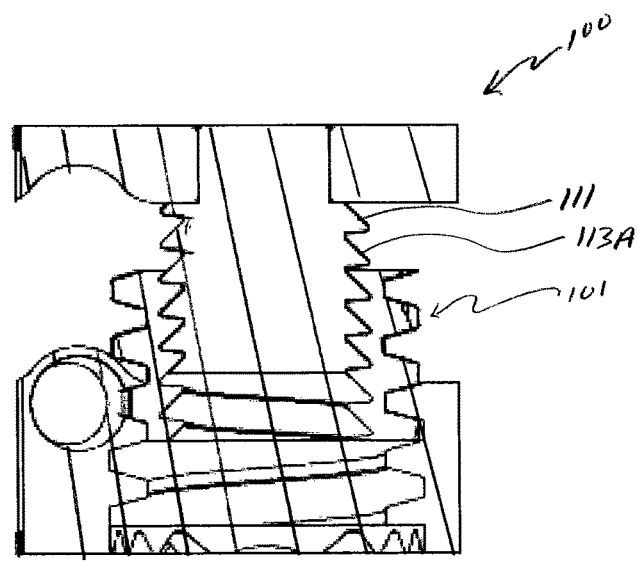
FIG. 6B is a cross-sectional view of the device of FIG. 6A taken along the lines 6B-6B.
Figure 7A:
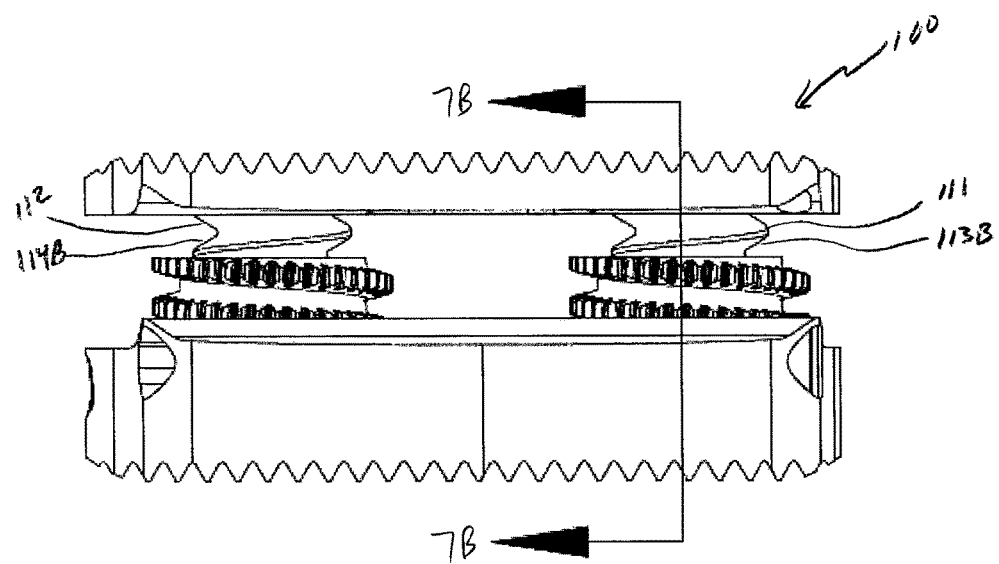
FIG. 7A is a front view of a a device employing a coaxial screw gear sleeve mechanism according to an embodiment of the present invention.
Figure 7B:
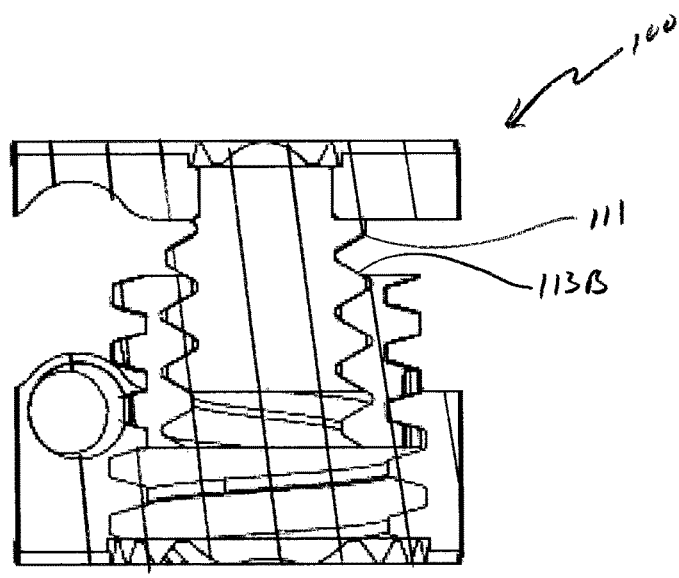
FIG. 7B is a cross-sectional view of the device of FIG. 7A taken along the lines 7B-7B.

FIGS. 6A and 6B depict another embodiment of the present invention where in threaded posts 111, 112 employ a buttress thread 113A, 114A (compare threads 113A in FIG. 6B to threads 113, 114 in FIG. 1D). A buttress thread configuration results in the load bearing thread face being perpendicular to the screw axis of the post 111, 112, which increases the axial strength of the coaxial screw gear sleeve mechanisms. FIGS. 7A and 7B depict a further embodiment that utilizes a standard 60 degree thread 113B, 114B on threaded posts 111, 112. 60 degree threads are considered industry standard and can therefore be created with common machining practices. This can result in a device that can be more quickly and inexpensively produced.

Figure 8A:
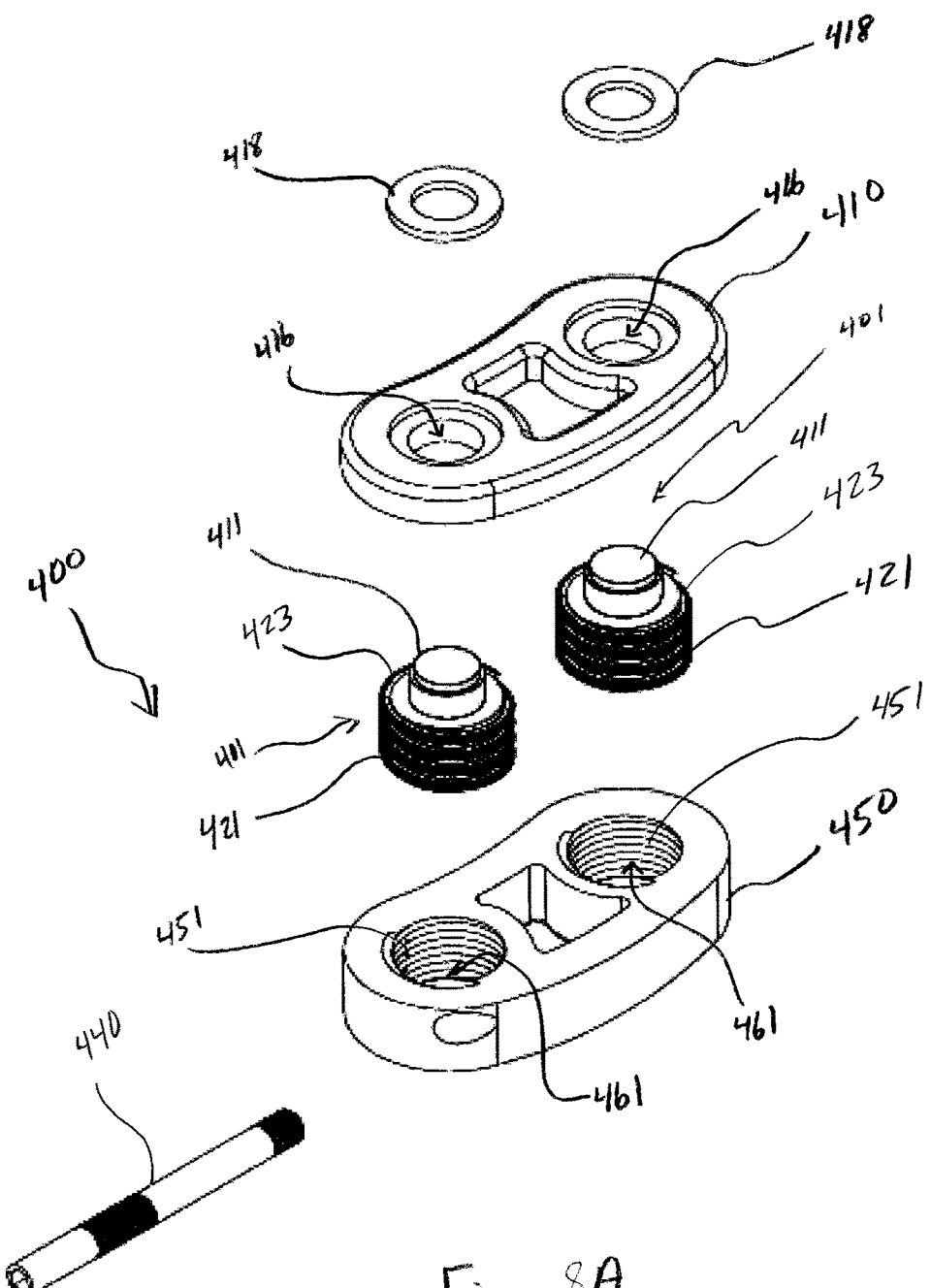
FIG. 8A is an exploded view of a device employing a coaxial screw gear sleeve mechanism according to an embodiment of the present invention.
Figure 8B:
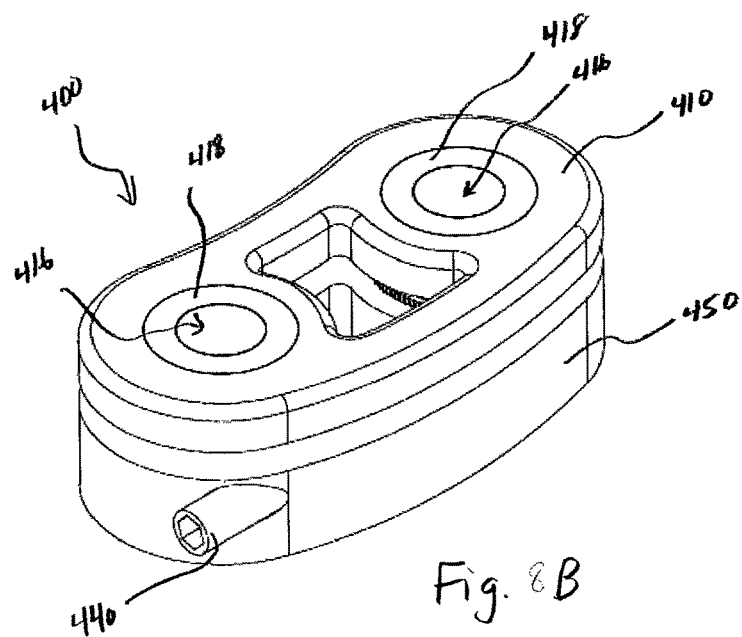
FIG. 8B is a perspective view of the device of FIG. 8A.
Figure 8C:
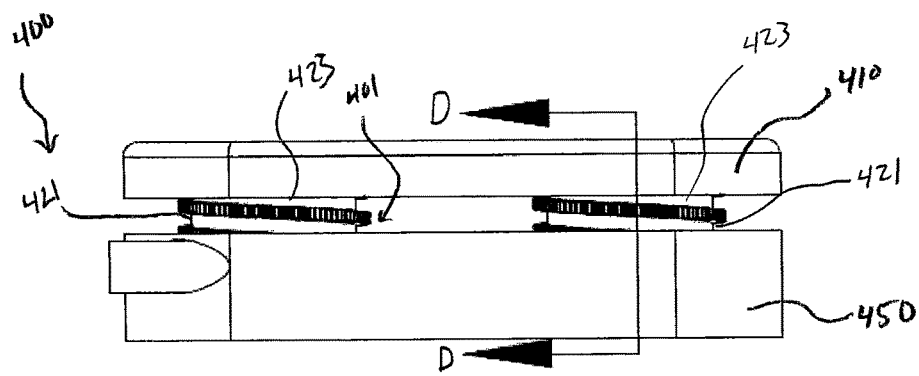
FIG. 8C is a front view of the device of FIG. 8A.
Figure 8D:
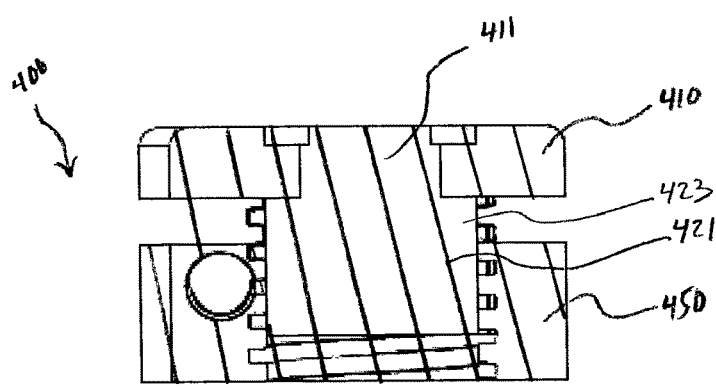
FIG. 8D is a cross-sectional view of the device of FIG. 8A taken along the lines 8D-8D in FIG. 8C.
Figure 9A:
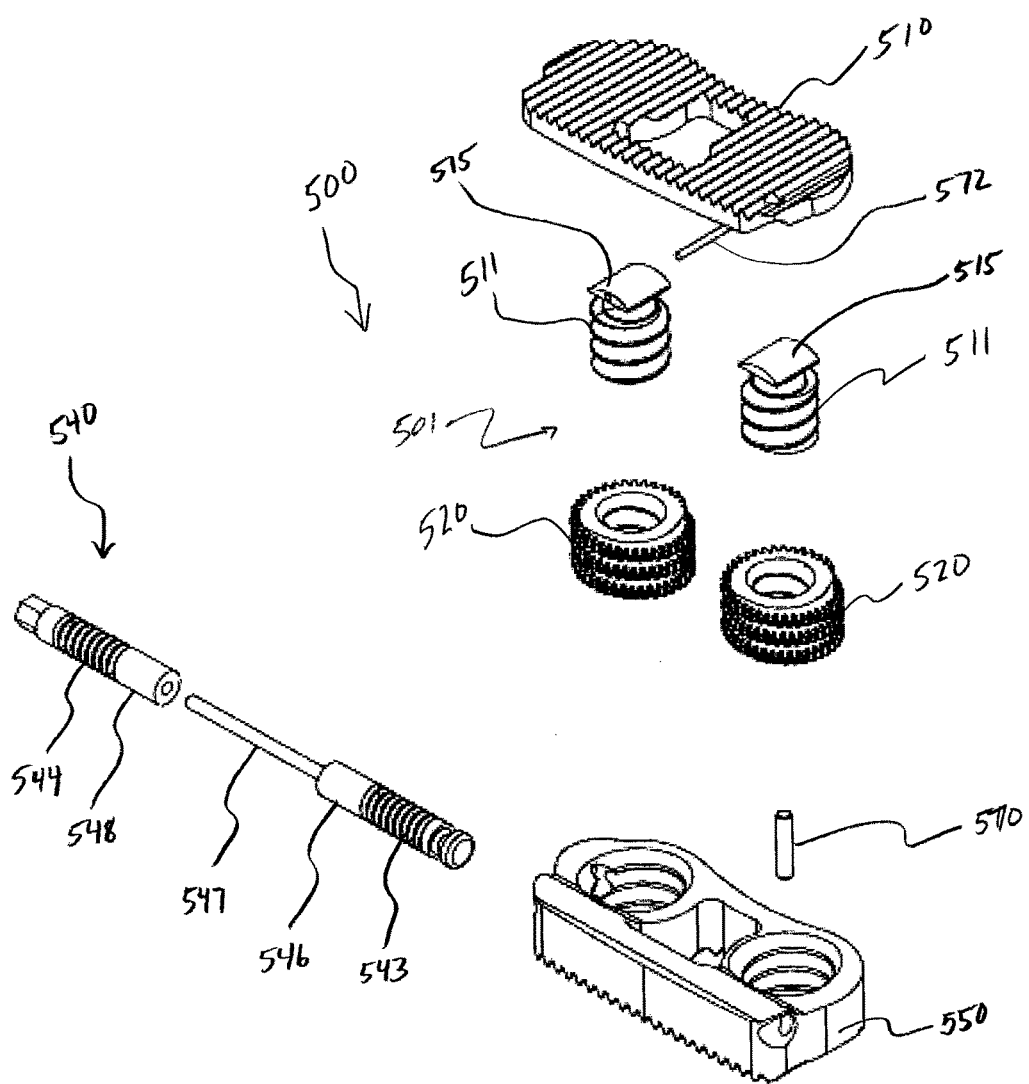
FIG. 9A is an exploded view of a device employing a coaxial screw gear sleeve mechanism according to an embodiment of the present invention.
Figure 9B:
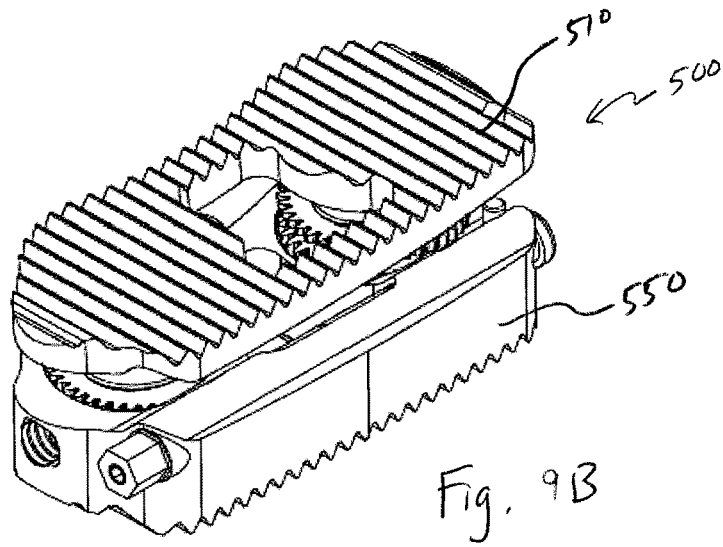
FIG. 9B is a perspective view of the device of FIG. 9A.
Figure 9C:
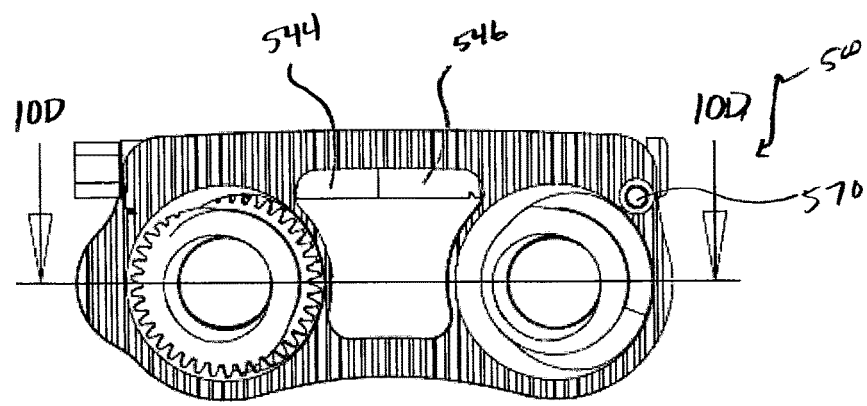
FIG. 9C is a bottom view of the device of FIG. 9A.
Figure 9D:
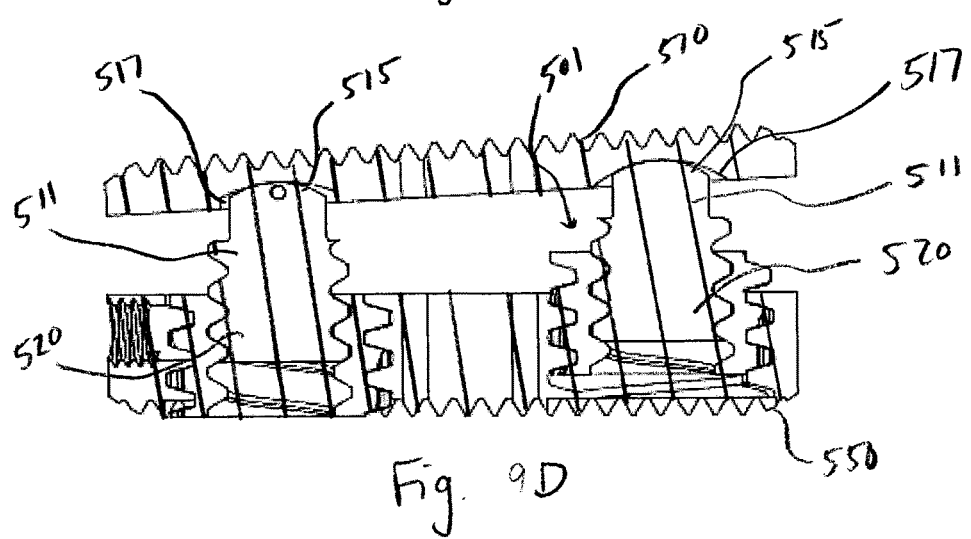
FIG. 9D is a cross-sectional view of the device of FIG. 9A taken along the lines 9D-9D in FIG. 9C.

Referring now to FIGS. 8A-8D, another expandable device 400 includes a pair of coaxial screw gear sleeve mechanisms 401 comprising threaded geared posts 423 extending between first member 410 and second member 450 rather than the separate threaded geared sleeves 120, 130 and threaded posts 111,112 described previously. Threaded geared posts 423 each include a threaded geared portion 421 and a post portion 411. Threaded geared portions 421 fit within openings 461 in second member 450 and interface with worm 440 and internal threads 451 to cause the device 400 to expand or lift. Post portions 411 fit within openings 416 in first member 410 and can be attached to washers 418. Washers 418 keep the first member 410 in place relative to the threaded geared posts 423 as the threaded geared posts 423 rotate freely independent of the first member 410 when the device 400 is actuated. Thus, as seen in FIGS. 8C and 8D, the expansion between the first member 410 and the second member 450 is caused by the thicker threaded geared portions 421 while the post portions 411 remain within the openings 416 in first member 410. This leads to a device 400 having increased axial strength.

FIGS. 9A-9D depict a further embodiment of an expandable device 500 utilizing coaxial screw gear sleeve mechanisms 501 that allows for differential adjustment of the threaded geared sleeves 520. Threaded posts 511 can each include an arched portion 515 that corresponds to an arched recess 517 in first member 510. The arched interface between the threaded posts 511 and the first member 510 created by the corresponding arched portions 515 and arched recesses 517 allows the first member 510 to rotate and become angled relative to the second member 550. A pin joint utilizing a pivot pin 572 can be used to keep one interface between the first member 510 and a threaded post 511 stationary, while the other interface is allowed to slide due to the arched surfaces. A placement pin 570 is used to prevent the worm 540 from sliding out of the second member 550 when expanding the device. Worm 540 can be a two-part worm including a first portion 546 having a first threaded section 543 and second portion 548 having a second threaded section 544 that fits onto a post 547 of first portion 546. The two portions 546, 548 can therefore be rotated independently of each other, with each driving a separate threaded geared sleeve 520. Because each threaded geared sleeve 520 can be engaged separately, they can be expanded by different amounts, resulting in an angled first member 510 as shown most clearly in FIG. 9D. Optionally, the arched recesses 517 in the first member 550 and arched surfaces 515 of the posts 511 could be replaced with flexural joints or ball or cylinder and socket joints.

Figure 10A:
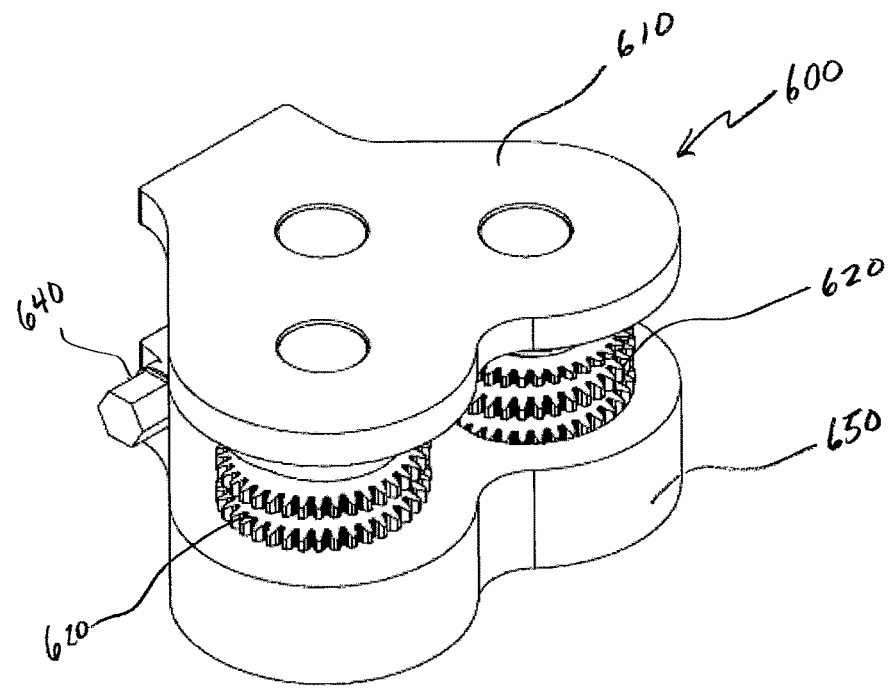
FIG. 10A is a perspective view of a device employing a coaxial screw gear sleeve mechanism according to an embodiment of the present invention.
Figure 10B:
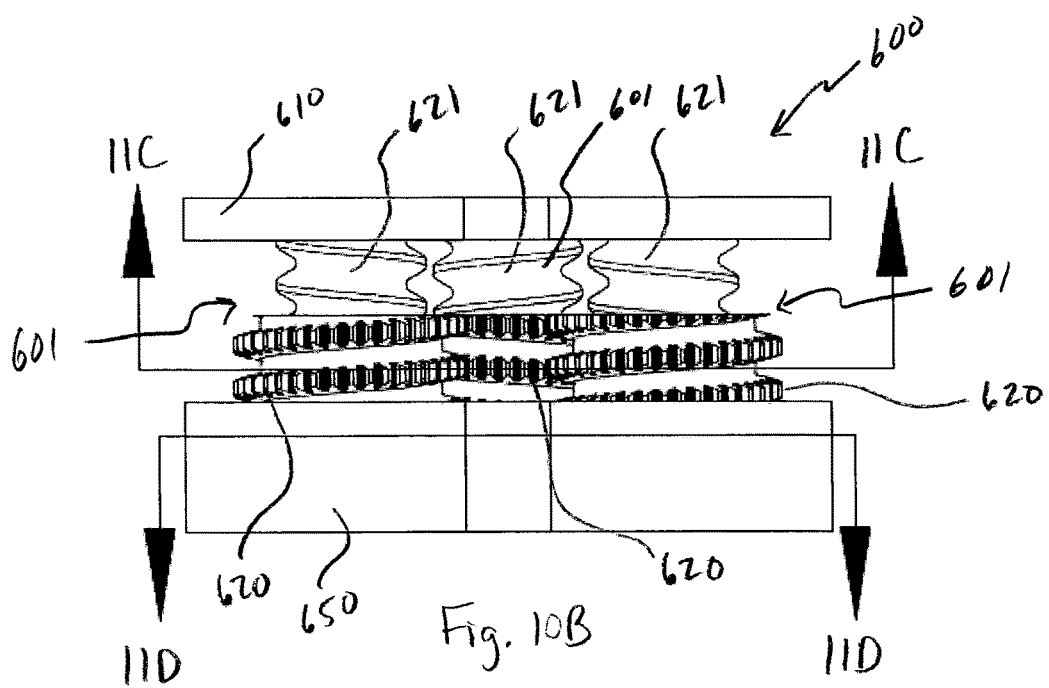
FIG. 10B is a front view of the device of FIG. 10A.
Figure 10C:
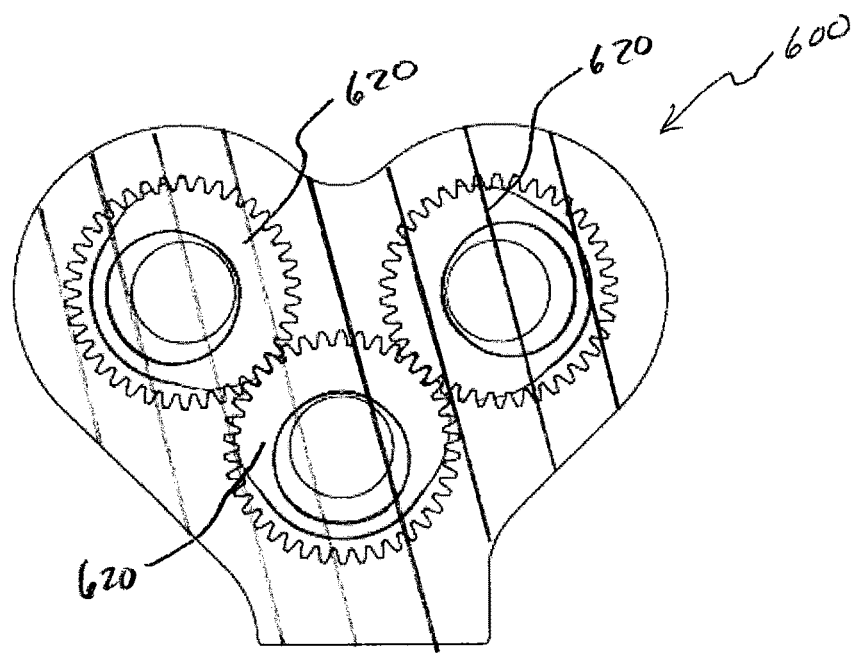
FIG. 10C is a cross-sectional view of the device of FIG. 10A taken along the lines 10C-10C in FIG. 10B.
Figure 10D:
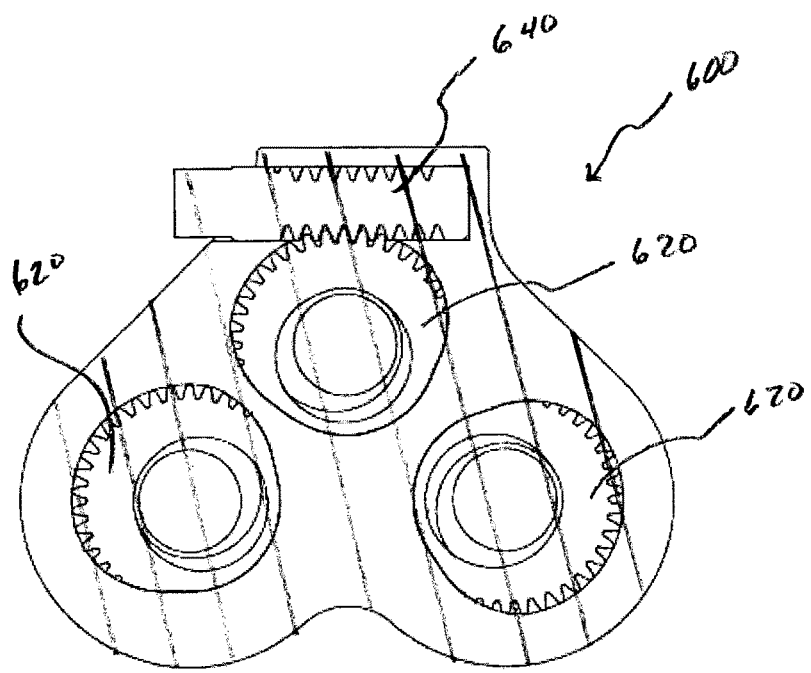
FIG. 10D is a cross-sectional view of the device of FIG. 10A taken along the lines 10D-10D in FIG. 10B.

An expandable device 600 according to another embodiment of the present invention is depicted in FIGS. 10A-10D. Device 600 uses three coaxial screw gear sleeve mechanisms 601, each having a threaded geared sleeve 620 and a threaded post 621, between first member 610 and second member 650. As seen in FIGS. 10C and 10D, to expand or lift the device, the worm drive 640 is rotated and it engages one of the threaded geared sleeves 620, causing it to rotate. As the first threaded geared sleeve 620 rotates, it engages the other two threaded geared sleeves 620, causing them to rotate and the device 600 to expand. The rotation of the threaded geared sleeves 620 also causes the threaded posts 621 to expand, as described previously. Use of three coaxial screw gear sleeve mechanisms provides for a device having increased strength in the axial direction and a broader surface area for supporting loads. Optionally, each of the three expansion mechanisms could be actuated independently to adjust the surface of the device in additional degrees of freedom.

Figure 11A:
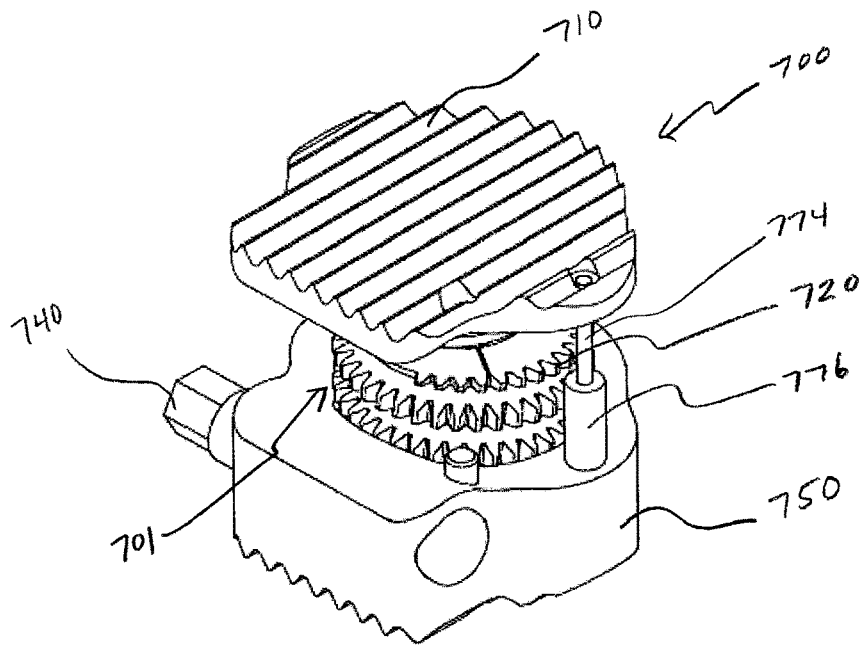
FIG. 11A is a perspective view of a device employing a coaxial screw gear sleeve mechanism according to an embodiment of the present invention.
Figure 11B:
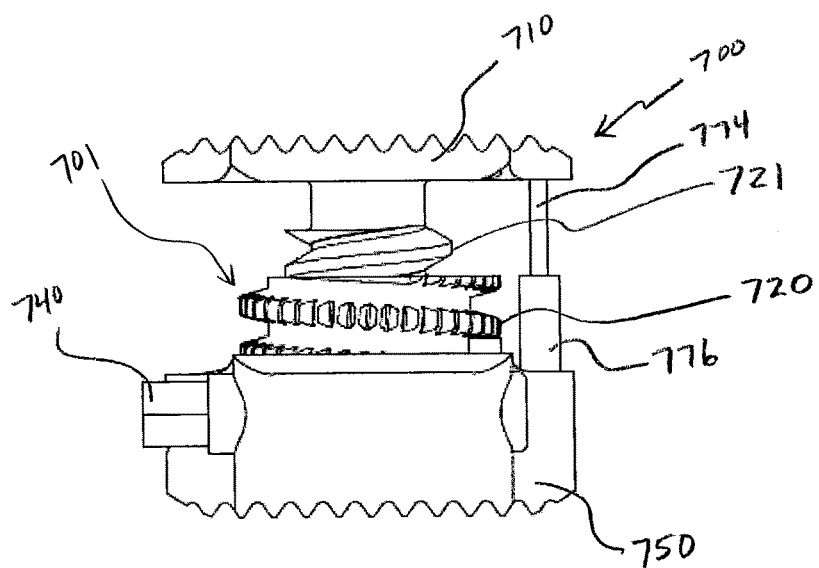
FIG. 11B is a side view of the device of FIG. 11A.
Figure 12A:
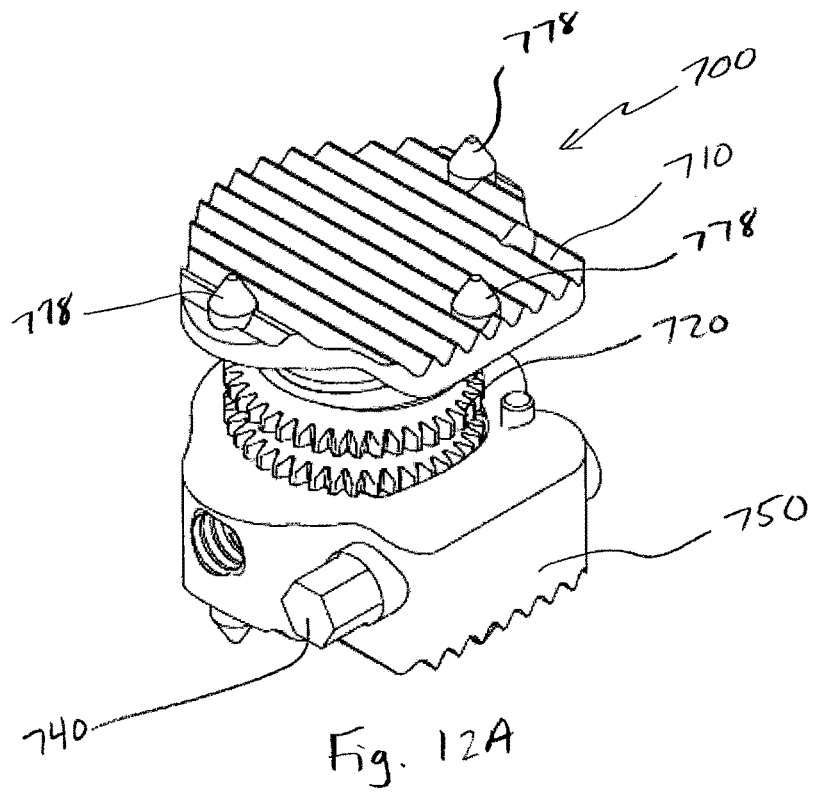
FIG. 12A is a perspective view of a device employing a coaxial screw gear sleeve mechanism according to an embodiment of the present invention.
Figure 12B:
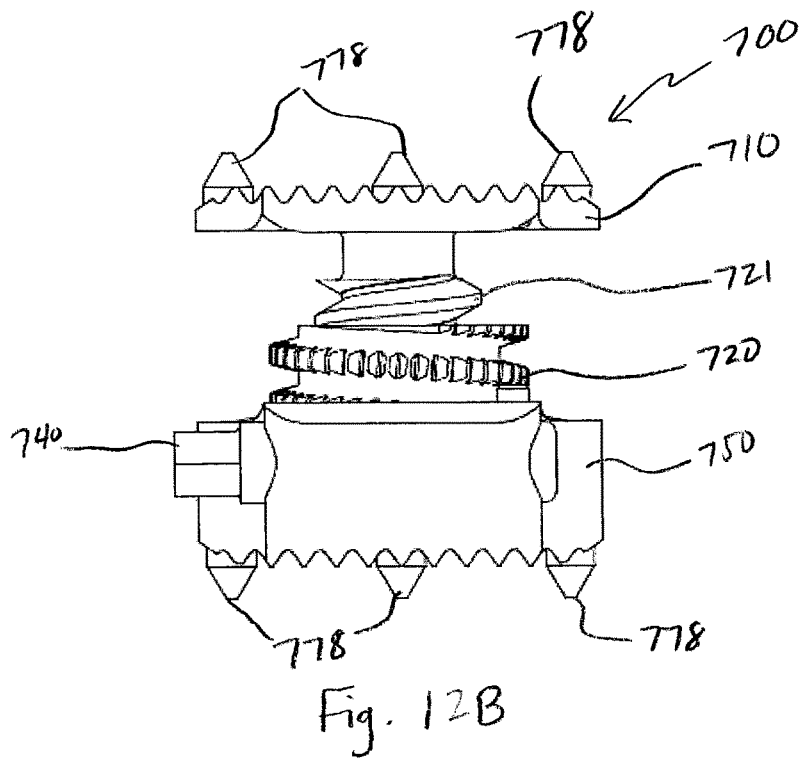
FIG. 12B is a side view of the device of FIG. 12A.
Figure 13A:
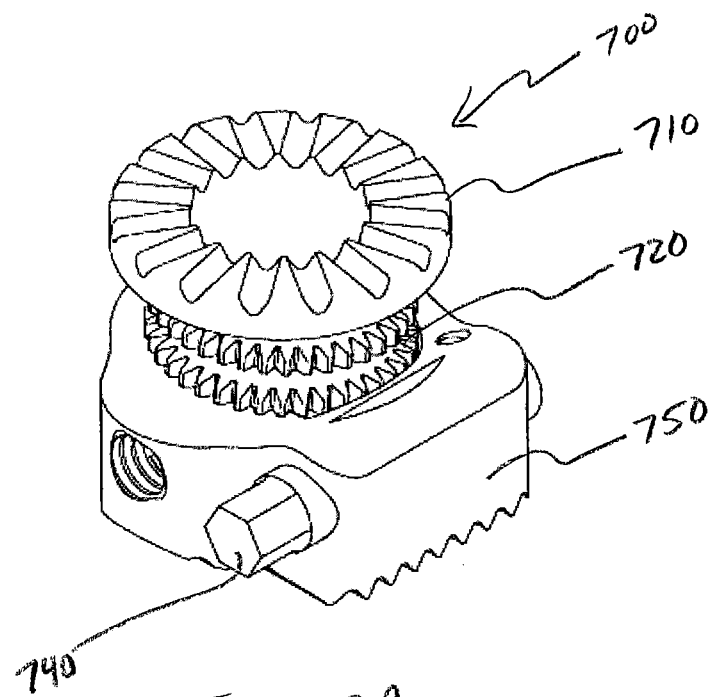
FIG. 13A is a perspective view of a device employing a coaxial screw gear sleeve mechanism according to an embodiment of the present invention.
Figure 13B:
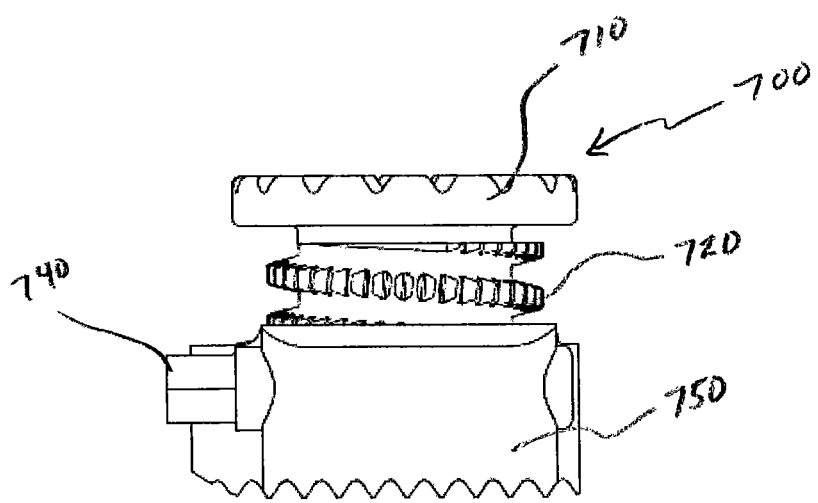
FIG. 13B is a side view of the device of FIG. 13A.

FIGS. 11A and 11B depict a device 700 that employs only a single coaxial screw gear mechanism 701 having a threaded geared sleeve 720 and a threaded post 721 for expanding first member 710 relative to second member 750 with worm 740. Device 700 also can include first 774 and second 776 telescoping support elements. Telescoping support elements 774, 776 serve to maintain the relative rotational positioning of the first member 710 with respect to the second member 750, enabling the threaded geared sleeve 720 to rotate with respect to both the first member 710 and second member 750 to expand the device 700. FIGS. 12A and 12B depict a further variation of device 700 that utilizes a plurality of spikes 778 extending from the first member 710 and second member 750 to rotationally constrain the first member 710 and second member 750. In operation, the spikes 778 contact adjacent surfaces and can fix themselves to those surfaces to prevent the first member 710 and second member 750 from rotating relative to each other. A further embodiment is depicted in FIGS. 13A and 13B. This embodiment includes a coaxial screw gear sleeve mechanism having only a threaded geared sleeve 720 between first member 710 and second member 750 and allows the first member 710 to rotate with the sleeve 720 as the device 700 is expanded via rotation of the worm 740. Optionally, first member 710 could be rotationally free with respect to the threaded geared sleeve 720 so that the first member 710 is allowed to engage and not rotate against an adjacent surface.

Figure 14B:
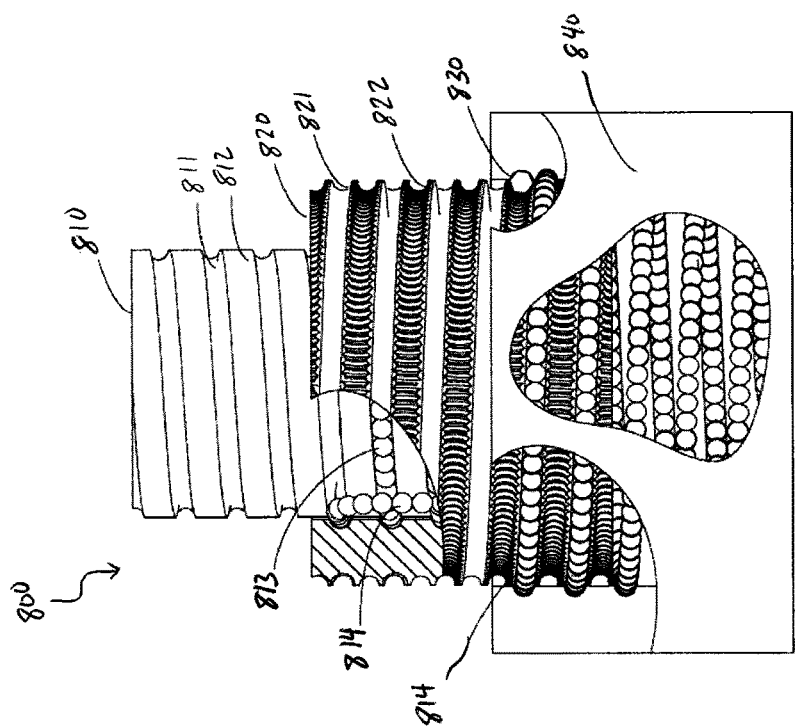
FIG. 14B is a partial cutaway view of the device of FIG. 14A.
Figure 14A:
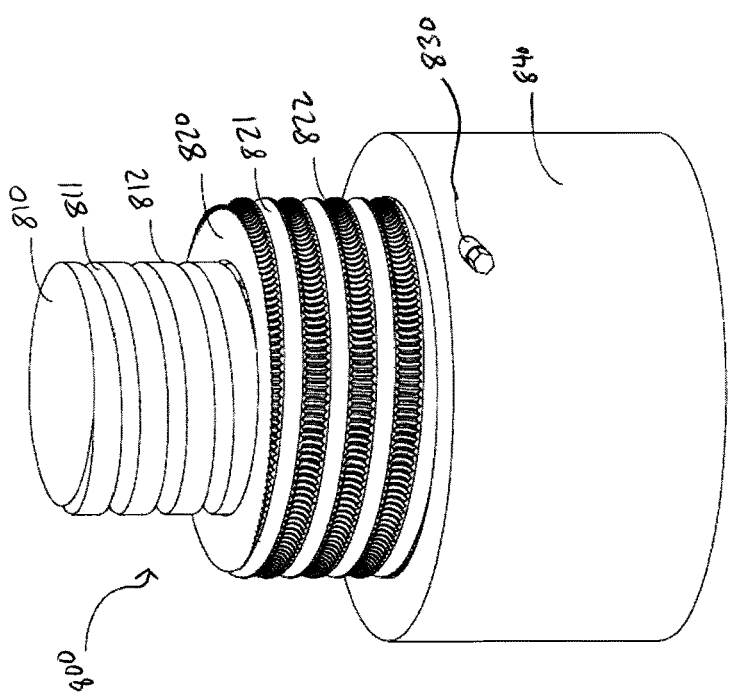
FIG. 14A is a perspective view of an expandable device employing a coaxial screw gear sleeve mechanism according to an embodiment of the present invention.

FIGS. 14A and 14B depict an expandable device 800 including an enveloping coaxial screw gear sleeve with recirculating bearings according to another embodiment of the present invention. Device 800 includes a post 810, an enveloping coaxial screw gear sleeve 820, a worm 830 and a housing 840. Post 810 includes a smooth outer surface 812 and a machined helical raceway 811 for bearings 813. A helical raceway (not shown) is also machined into inner surface of enveloping coaxial screw gear sleeve 820 that is complementary to helical raceway 811 for accommodating bearings 813. The inner surface of coaxial screw gear sleeve 820 also includes a machined tunnel for recirculation of bearings 813 as the post 810 moves with respect to the sleeve 820. The recirculating bearings are depicted as bearings 814 in FIG. 14B. The outer surface of the enveloping coaxial screw gear sleeve also includes a helical raceway 821 for recirculating bearings 814 and an enveloping screw gear 822. The worm 830 has a helical thread configured to engage the enveloping screw gear 822 of the sleeve 820. The inner surface of the housing 840 has a helical raceway (not shown) that cooperates with helical raceway 821 to retain bearings 814 and a tunnel for recirculating bearings 814 as the coaxial screw gear sleeve 820 moves with respect to the housing 840.

To expand the device 800, the worm 830 is rotated clockwise to engage the enveloping screw gear 822 to rotate and translate the enveloping coaxial screw gear sleeve 820 out of the housing 840. This simultaneously causes the post 810 to translate (but not rotate) out of the enveloping coaxial screw gear sleeve 820 and away from the housing 840. Bearings 813, 814 enable the rotation of the enveloping coaxial screw gear sleeve 820 with very little friction, enabling the device 800 to exhibit a very high mechanical advantage and displacement control with very high resolution. The use of the enveloping screw gear 822 enables the interface between the worm 830 and the enveloping coaxial screw gear sleeve 820 to carry substantially higher loading.

Referring now to FIGS. 15A-15D, there can be seen another expandable device 900 utilizing a coaxial screw gear sleeve according to an embodiment of the present invention. Device 900 includes an enveloping coaxial screw gear 910, a housing 920 and a worm 930. The outer surface of enveloping coaxial screw gear sleeve 910 includes a helical groove having a series of enveloping coaxial screw gear teeth 914. The helical groove can cooperate with an internal thread 921 on the inner surface 922 of housing 920 to allow the device 900 to carry an axial load. In another embodiment, the gear teeth 914 can be machined directly into the outer surface of the enveloping coaxial screw gear sleeve 910. In one embodiment, the outer surface of the enveloping coaxial screw gear sleeve 910 can be a smooth machined surface that acts like a bearing surface when configured with a similar smooth bearing surface on the inner surface 922 of housing 920 to enable the device 900 to carry a lateral load. Optionally, the coaxial screw gear sleeve 920 could have recirculating bearings both on the inside and the outside of the sleeve and the recirculation tunnel could be between the inside and the outside of the sleeve, both facilitating assembly and manufacturing.

To expand the device 900, the worm 930 is rotated to engage the enveloping coaxial screw gear teeth 914 to rotate and translate the enveloping coaxial screw gear sleeve 910 with respect to the housing 920. In one embodiment, the inner surface 910 and center bore 912 can be configured to contain a post similar to the post 910 described in FIGS. 14A and 14B to compound the expansion or lift of the device. In one embodiment, no thread 921 is present on the inner surface 922 of housing 920, so the helical groove and/or gear teeth 914 of the enveloping coxial screw gear sleeve 910 cause the sleeve 910 to translate with respect to the housing 930 as the sleeve 910 rotates. In such a configuration, the worm 930 would carry any axial load, unassisted by an inclined interface between the enveloping coaxial screw gear sleeve 910 and the housing 920.

Coaxial screw gear sleeve mechanisms as described herein can be made out of any material, including metals, plastics and ceramics. In one embodiment, coaxial screw gear sleeve mechanisms as described herein can be made of titanium. In other embodiments mechanisms can be made from cobalt chrome, MP35N, PEEK, stainless steel, or carbon fiber.

Coaxial screw gear sleeve mechanisms can be manufactured in various ways. In one embodiment, thread milling can be implemented to manufacture the various threads in device. Wire EDM can be utilized to manufacture some or all of the holes and openings in the device. Assembly jigs and post processing steps can also be utilized to allow the device to be manufactured to exacting standards.

Various embodiments of systems, devices, and methods have been described herein. These embodiments are given only by way of example and are not intended to limit the scope of the present invention. It should be appreciated, moreover, that the various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the invention.

The invention claimed is:

1. A lifting mechanism comprising:
a base member having an inner surface;
an upper member having an inner surface configured to face the inner surface of the base member;
a size-adjustable support engaging the base member and the upper member to provide an adjustable expansion height of the upper member with respect to the base member, the size-adjustable support comprising:
a first post;
a second post, each of the first and second posts non-rotatably extending from the upper member and having a threaded exterior surface;
a first sleeve configured to surround the first post; and
a second sleeve configured to surround the second post, each sleeve having a threaded interior surface configured to directly interface with the threaded exterior surface of the corresponding first or second post, and a helically geared exterior surface; and
a drive mechanism having a surface configured to interface with and drive the helically geared exterior surfaces of the first and second sleeves, such that selective operation of the drive mechanism telescopically expands the upper member with respect to the base member by the first sleeve and the second sleeve axially translating relative to the base member simultaneously with the first post and the second post translating relative to the first sleeve and the second sleeve.

2. The lifting mechanism of claim 1, wherein the drive mechanism is a worm drive having a pair of threaded sections, each threaded section configured to interface with only one of the first and second sleeves when the drive mechanism is operated.

3. The lifting mechanism of claim 1, wherein the base member includes a unitary body defining a pair of sleeve openings in the inner surface, each sleeve opening sized to rotatingly accommodate one of the first or second sleeves therein.

4. The lifting mechanism of claim 1, wherein the base member includes a unitary body defining a drive mechanism aperture sized to rotatingly contain the drive mechanism therein.

5. The lifting mechanism of claim 4, wherein the drive mechanism interfaces with the first sleeve and the second sleeve through respective sleeve openings in the unitary body between the drive mechanism aperture and the respective first and second sleeves.

6. The lifting mechanism of claim 1, wherein the inner surface of the base member and the inner surface of the upper member are configured to contact each other when the size-adjustable support is at a minimum expansion.

7. The lifting mechanism of claim 1, wherein the threaded interior surface and the helically geared exterior surface of each sleeve are formed on unitary bodies of the respective first and second sleeves.

8. The lifting mechanism of claim 1, wherein the base member and the upper member each have a length that is greater than a height of the lifting mechanism when the lifting mechanism is in a compressed state.

9. A lifting mechanism comprising:
a base member having an inner surface;
an upper member having an inner surface configured to face the inner surface of the base member;
a first coaxial screw gear sleeve mechanism and a second coaxial screw gear sleeve mechanism movable between the base member and the upper member, each coaxial screw gear sleeve mechanism comprising:
a post having a threaded exterior surface, the post non-rotatably secured with the upper member; and
a sleeve configured to surround the post, the sleeve having a threaded interior surface configured to directly interface with the threaded exterior surface of the post, and a helically geared exterior surface; and
a drive mechanism having a surface configured to interface with and drive the helically geared exterior surfaces of the sleeves, such that selective operation of the drive mechanism telescopically expands the upper member with respect to the base member by the sleeves axially translating relative to the base member simultaneously with the first post and the second post translating relative to the first sleeve and the second sleeve.

10. The lifting mechanism of claim 9, wherein the drive mechanism is a worm drive having a pair of threaded sections, each threaded section configured to interface with only one of the sleeves when the drive mechanism is operated.

11. The lifting mechanism of claim 9, wherein the base member includes a unitary body defining a pair of sleeve openings in the inner surface, each sleeve opening sized to rotatingly accommodate one of the sleeves therein.

12. The lifting mechanism of claim 9, wherein the base member includes a unitary body defining a drive mechanism aperture sized to rotatingly contain the drive mechanism therein.

13. The lifting mechanism of claim 12, wherein the drive mechanism interfaces with the sleeves through respective sleeve openings in the unitary body between the drive mechanism aperture and the respective sleeves.

14. The lifting mechanism of claim 9, wherein the inner surface of the base member and the inner surface of the upper member are configured to contact each other when the first and second coaxial screw gear sleeve mechanisms are at a minimum expansion.

15. The lifting mechanism of claim 9, wherein the threaded interior surface and the helically geared exterior surface of each sleeve are formed on a unitary body of the respective sleeve.

16. The lifting mechanism of claim 9, wherein the base member and the upper member each have a length that is greater than a height of the lifting mechanism when the lifting mechanism is in a compressed state.

17. A lifting mechanism comprising:
a base; and
a size-adjustable support configured to be adjustably expanded with respect to the base member, the size-adjustable support comprising:
a first post and a second post each having a threaded exterior surface, at least one post of the first or second posts being non-rotatable;
a first sleeve configured to surround the first post;
a second sleeve configured to surround the second post, each sleeve having a threaded interior surface configured to directly interface with the threaded exterior surface of the corresponding post, and a helically geared exterior surface; and
a drive mechanism having a surface configured to interface with and drive the helically geared exterior surfaces of the first and second sleeves, such that selective operation of the drive mechanism telescopically expands the size-adjustable support with respect to the base member by the first sleeve and the second sleeve axially translating relative to the base member simultaneously with the first post and the second post translating relative to the first sleeve and the second sleeve.

18. The lifting mechanism of claim 17, wherein the drive mechanism is a worm drive having a pair of threaded sections, each threaded section configured to interface with only one of the first and second sleeves when the drive mechanism is operated.

19. The lifting mechanism of claim 17, wherein the base member includes a unitary body defining a pair of sleeve openings in the inner surface, each sleeve opening sized to rotatingly accommodate one of the first and second sleeves therein.

20. The lifting mechanism of claim 19, wherein the base member includes a unitary body defining a drive mechanism aperture sized to rotatingly contain the drive mechanism therein.

21. The lifting mechanism of claim 17, wherein the size-adjustable support is transitionable relative to the base between a first position, in which, the size-adjustable support engages the base, and a second position, in which, the size-adjustable support is spaced apart from the base.

22. The lifting mechanism of claim 21, wherein the first and second sleeves are disposed within the base when the size-adjustable support is in the first position.

23. The lifting mechanism of claim 21, wherein at least a portion of the first or second sleeves is configured to extend out of the base when the size-adjustable support is in the second position.

* * * * *